United States Patent
Blassnig et al.

(10) Patent No.: US 9,544,577 B2
(45) Date of Patent: Jan. 10, 2017

(54) METHOD OF CAPTURING THREE-DIMENSIONAL (3D) INFORMATION ON A STRUCTURE

(71) Applicants: Andreas Blassnig, Klagenfurt (AT); Helmut Angerer, Klagenfurt (AT); Engelbert Kelz, Klagenfurt (AT); Christian Zinner, Vienna (AT); Stephan Thierjung, Vienna (AT); Christoph Nowak, Vienna (AT); Jurgen Jesenko, Finkenstein (AT); Horst Koinig, Klagenfurt (AT)

(72) Inventors: Andreas Blassnig, Klagenfurt (AT); Helmut Angerer, Klagenfurt (AT); Engelbert Kelz, Klagenfurt (AT); Christian Zinner, Vienna (AT); Stephan Thierjung, Vienna (AT); Christoph Nowak, Vienna (AT); Jurgen Jesenko, Finkenstein (AT); Horst Koinig, Klagenfurt (AT)

(73) Assignee: A.TRON3D GMBH, Klagenfurt am Worthersee (AT)

( * ) Notice: Subject to any disclaimer, the term of this patent is extended or adjusted under 35 U.S.C. 154(b) by 344 days.

(21) Appl. No.: 14/334,729

(22) Filed: Jul. 18, 2014

(65) Prior Publication Data
US 2015/0022639 A1    Jan. 22, 2015

Related U.S. Application Data

(60) Provisional application No. 61/847,712, filed on Jul. 18, 2013.

(51) Int. Cl.
*H04N 13/02* (2006.01)
*G06T 15/06* (2011.01)
(Continued)

(52) U.S. Cl.
CPC ......... *H04N 13/0275* (2013.01); *A61B 5/0088* (2013.01); *A61C 19/04* (2013.01);
(Continued)

(58) Field of Classification Search
CPC ............ H04N 13/0275; H04N 13/0051; H04N 13/0239; H04N 13/0221; H04N 13/0253; H04N 5/2256; H04N 2013/0081; G06T 15/06; G06T 15/08; G06T 15/205; G06T 19/20; G06T 7/0012; G06T 7/0071; G06T 17/00; G06T 2207/10028; G06T 2207/30026; A61C 19/04; A61B 5/0088; G01B 11/2513; G01B 2210/52
(Continued)

(56) References Cited

U.S. PATENT DOCUMENTS

| | | | | |
|---|---|---|---|---|
| 2011/0267344 A1* | 11/2011 | Germann | ........... | G06K 9/00201 345/420 |
| 2012/0045091 A1* | 2/2012 | Kaganovich | .......... | G06T 7/0071 382/103 |
| 2013/0241928 A1* | 9/2013 | Brown | ................. | G06T 19/006 345/420 |

OTHER PUBLICATIONS

Frey, Philip, "Raycasting von adaptiven Isoflachen", 2005, Computer Graphics Laboratory, pp. ii-vii, and 1-30; English abstract is provided on p. v.
(Continued)

*Primary Examiner* — Allen Wong
(74) *Attorney, Agent, or Firm* — Young & Thompson

(57) ABSTRACT

A method of capturing three-dimensional (3D) information on a structure includes obtaining a first image set containing images of the structure with at least one physical camera located at a first position, the first image set comprising one or more images; reconstructing 3D information from the first image set; obtaining 3D information from a virtual camera out of an existing global model of the structure; determining
(Continued)

correspondences between the obtained 3D information and the reconstructed 3D information; determining camera motion between the obtained 3D information and the reconstructed 3D information from the correspondences; and updating the existing global model by entering the obtained 3D information using the determined camera motion.

16 Claims, 10 Drawing Sheets

(51) Int. Cl.
    *G06T 19/20*     (2011.01)
    *A61C 19/04*     (2006.01)
    *G06T 7/00*     (2006.01)
    *G06T 15/08*     (2011.01)
    *G06T 17/00*     (2006.01)
    *H04N 5/225*     (2006.01)
    *H04N 13/00*     (2006.01)
    *A61B 5/00*     (2006.01)
    *G01B 11/25*     (2006.01)
    *G06T 15/20*     (2011.01)

(52) U.S. Cl.
    CPC ........ *G01B 11/2513* (2013.01); *G06T 7/0012* (2013.01); *G06T 7/0071* (2013.01); *G06T 15/06* (2013.01); *G06T 15/08* (2013.01); *G06T 15/205* (2013.01); *G06T 17/00* (2013.01); *G06T 19/20* (2013.01); *H04N 5/2256* (2013.01); *H04N 13/0051* (2013.01); *H04N 13/0221* (2013.01); *H04N 13/0239* (2013.01); *H04N 13/0253* (2013.01); *G01B 2210/52* (2013.01); *G06T 2207/10028* (2013.01); *G06T 2207/30036* (2013.01); *H04N 2013/0081* (2013.01)

(58) Field of Classification Search
    USPC .......................................................... 348/46
    See application file for complete search history.

(56) References Cited

OTHER PUBLICATIONS

Frisken et al., "Efficient Estimation of 3D Euclidean Distance Fields from 2D Range Images", Mitsubishi Electric Research Laboratories, www.merl.com, TR2002-34, Aug. 2002.
Hadwiger et al., "Real-Time Ray-Casting and Advanced Shading of Discrete Isosurfaces", Eurographics, 2005, vol. 24, No. 3.
Hagan et al., "Numerical Methods for Isosurface Volume Rendering", Virginia Tech, 2009, pp. 1-4.
Lorensen et al., "Marching Cubes: A High Resolution 3D Surface Construction Algorithm", Computer Graphics, Jul. 1987, vol. 21, No. 4, pp. 163-169.
Marmitt et al., "Fast and Accurate Ray-Voxel Intersection Techniques for Iso-Surface Ray Tracing", Stanford, USA, Nov. 16-18, 2004.
The I2C-Bus Specification, Version 2.1, Jan. 2000, Philips Semiconductors, pp. 1-46.
Sigg, Christian, "Representation and Rendering of Implicit Surfaces", A dissertation submitted to ETH Zurich No. 16664, 2006.
Tatarchuk et al., "Real-Time Isosurface Extraction Using the GPU Programmable Geometry Pipeline", Chapter 9, Advanced Real-Time Rendering in 3D Graphics and Games Course—SIGGRAPH 2007, pp. 122-137.
Tauer, Michael, "Implementation eines Raytracers innerhalb der 3D-Plattform GroIMP", Studienarbeit, Oct. 2006, pp. 1-42, Partial English translation is provided.
Muhlensiepen, Helga, "Visualisierung Von Magnetohydrodynamischen Daten", Nov. 2004, pp. 1-64, partial English translation is provided.
Han et al., "Combined Stereovision and Phase Shifting Method: Use of a Visibility-Modulated Fringe Pattern", Optical Measurement Systems for Industrial Inspection VI, vol. 7389, 73893H, 2009, XP55150328A.
Jang et al., "Structured-light stereo: Comparative analysis and integration of structured-light and active stereo for measuring dynamic shape", Optics and Lasers in Engineering, 2013, vol. 51, pp. 1255-1264.
Bach, Thanh Vi, "Seminararbeit GPU-Based Volume Ray Casting with Advanced Illumination", Year 2009, pp. 113-133; Partial English translation is provided.
Brent, Richard P., "Algorithms for Minimization Without Derivatives", Dover Publications, Inc., Year 2013, pp. 1-167.
Neubauer et al., "Cell-Based First-Hit Ray Casting", VRVis Research Center, Vienna, Austria, Year 2001.
Newcombe et al., "KinectFusion: Real-Time Dense Surface Mapping and Tracking", Microsoft Research, Year 2011.
Parker et al., "Interactive Ray Tracing for Isosurface Rendering", Computer Science Department, University of Utah, Year 1998.
Press et al., "Numerical Recipes in C++" The Art of Scientific Computing, Second Edition, Cambridge University Press, Year 2003, pp. 1-1002.
Rusinkiewicz et al., "Efficient Variants of the ICP Algorithm", Stanford University, Year 2001, pp. 1-8.
Samet et al., "Octree approximation and compression methods", IEEE Computer Society, Computer Science Department, University of Maryland, Year 2002, pp. 1-10.
"Visualization of Implicit Surfaces Using Adaptive Tetrahedrizations", Year 1997, pp. 1-17.
Choi et al., "Hybrid Approach for Accurate Depth Acquisition with Structured Light and Stereo Camera", Electronics and Telecommunications Research Institute (ETRI), XP 32222313A, Year 2012.
Brauer-Burchardt et al., "Phase unwrapping using geometric constraints for high-speed fringe projection based 3D measurements", Modeling Aspects in Optical Metrology IV, vol. 8789, 878906-1, XP55150324A, Year 2013.

\* cited by examiner (a) ray casting   (b) recursive ray tracing   (c) photon mapping

METHOD OF CAPTURING THREE-DIMENSIONAL (3D) INFORMATION ON A STRUCTURE

BACKGROUND OF THE INVENTION

In the following a specialized application and implementation of structured light computer vision and stereometric computer vision via suitable scanners is presented. The system is especially fit to capture three-dimensional information on natural as well as artificial intra-oral structures, such as teeth, jaw, gum, dental prosthesis, crowns, retainers and so on. The emphases are joining different depth-maps (eg.) from different views, resuming scans after interruption and improving the systems speed to achieve real-time scanning and representing on screen. By way of the present invention, a stereoscopic system is enhanced by employing structured light means.

BRIEF DESCRIPTION OF THE DRAWING FIGURES

Figure 16:
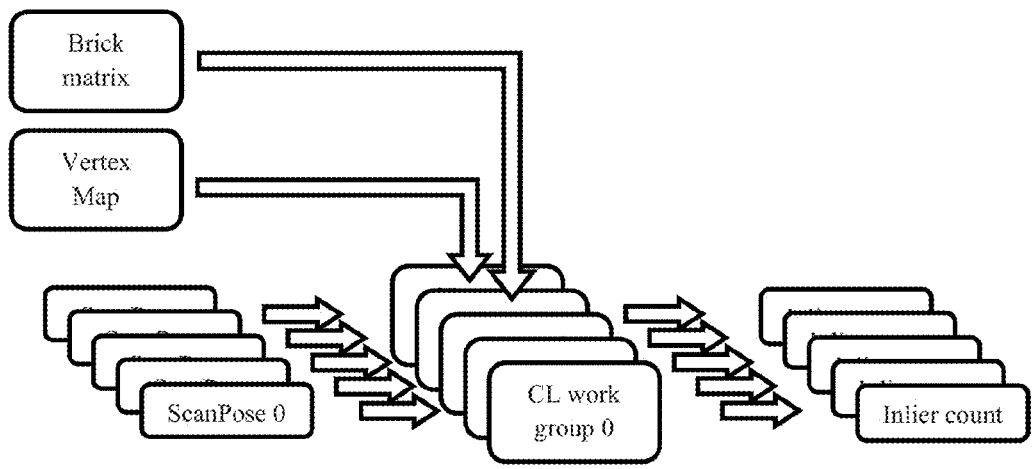

FIG. 16 relates to kernel execution.

Figure 17:
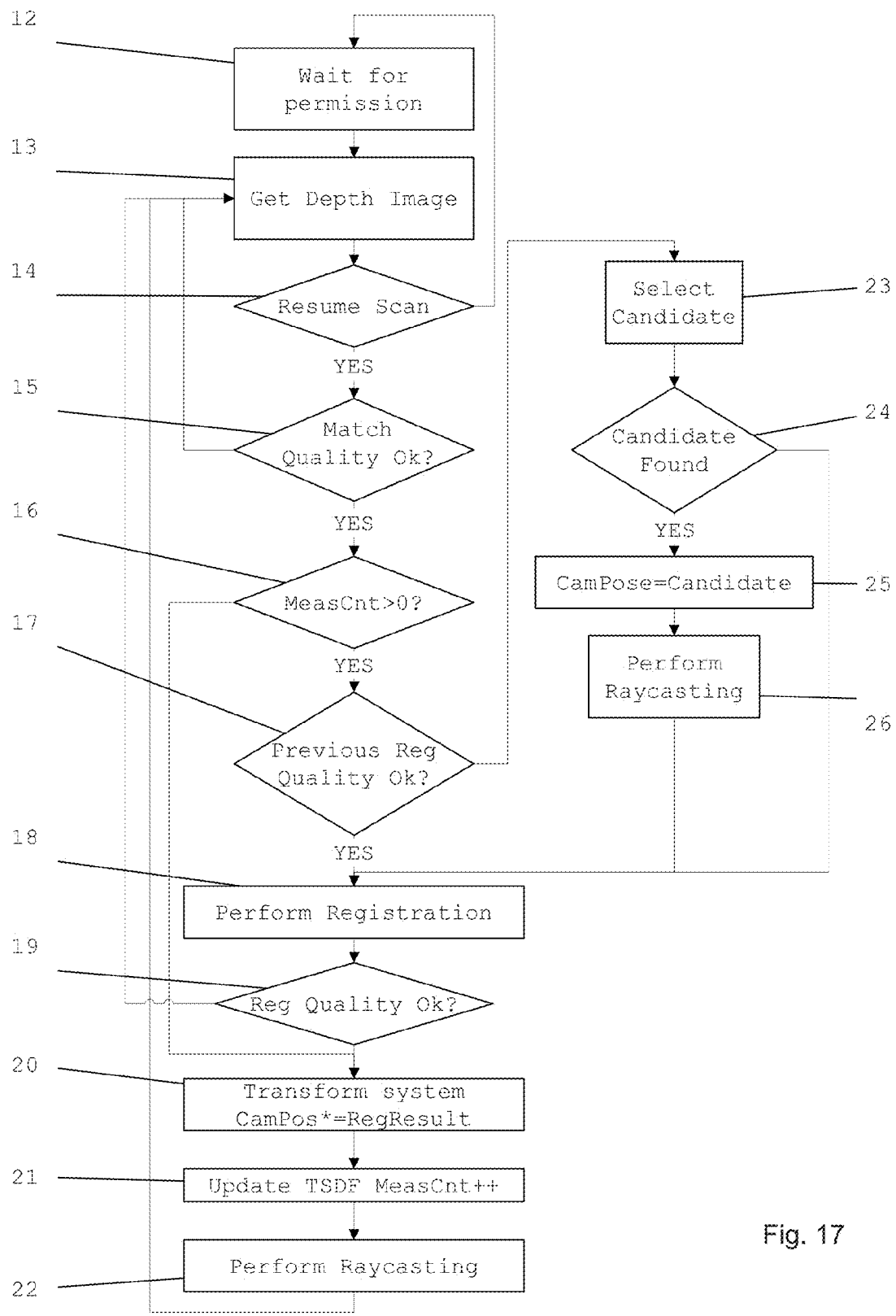

FIG. 17 shows a scan control thread.

Figure 18A:
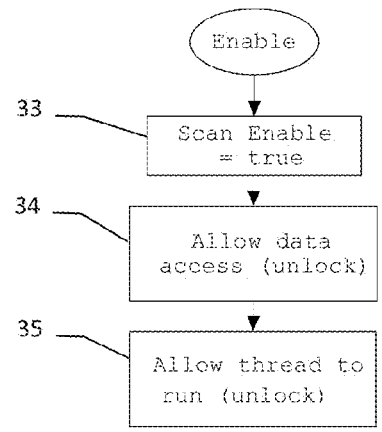
Figure 18:
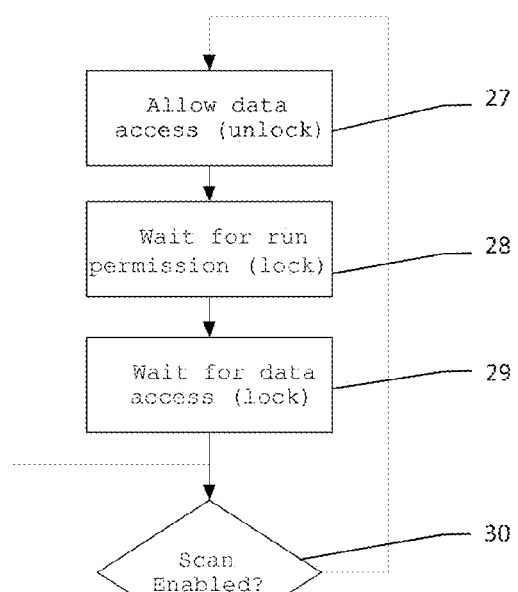

FIG. 18 shows an endless loop.

FIG. 18a shows scanning being enabled.

Figure 18B:
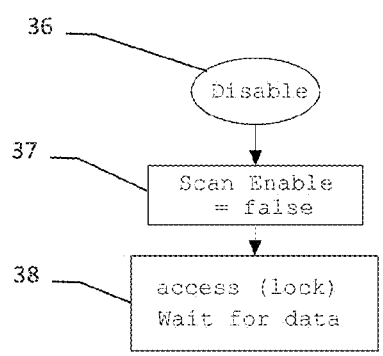

FIG. 18b shows scanning being resumed.

DESCRIPTION OF THE PREFERRED EMBODIMENTS

1. Introduction

The overall system of the presented intraoral scanner contains two main components:
handset+firmware; and
computer+computer software.

The functionality of the hand-held tool, which comprises essentially the projection of a light pattern onto the surface of the tooth and the gum and the chronologically synchronous recording of stereo image pairs and USB image data transfer, is achieved by optical, electronic/electrical and mechanical components and corresponding firmware for (at least) two USB controllers (manufacturer: Cypress) and also by a microcontroller (manufacturer: Amtel). The firmware ensures chronologically synchronous stereo image recording, sensor parameterization and USB data transfer (=video images, parameterization data, status values and measured values), and readout of the projector LED temperature, of the position sensor data, of a keystroke event and, for control purposes, of a tri-colored status LED (other means of optical feedback, like one-colored LED could also be employed). The communication between the USB controllers and the microcontroller is achieved via the serial $I^2C$ protocol [17]. The communication between the handset and computer is achieved via USB 2.0, although an upgrade to USB 3.0 can easily be achieved, as well as a downgrade to USB 1.0 can be implemented, although the latter would cause the system to be much weaker, especially slower. To overcome this weakness (at least partially), the "handset" is powered via USB. The PC software comprises the following software modules:

1. USB driver module as a data interface between "handset" and computer.
2. Software module for the bidirectional data exchange (=chronologically synchronous video image pairs, exposure time and amplification, projector LED temperature, optionally two further temperature values, position sensor data, three different states of the status LED, keystroke event, all relevant calibration data of the stereo camera, and parameters for individual PC software modules) between the PC software modules listed below and the "handset".
3. 3D measurement with $S^3E$ based on a camera/camera set-up and a camera/projector set-up (see Section 2) plus previously stored raw image data improvement (=initial set-up and continuous dark-frame subtraction for dark current compensation).

For a possible general layout of the "handset" see international patent publication WO 2012/126022 A1. The computer may comprise any standard state of the art technology since the presented intra oral scanner does not require any special hardware aside from the handset and the above mentioned.

2. S3E Stereo Software

In the case of 3D measurement of a scene using the $S^3E$ software module, at least two cameras and a light pattern projector having a previously known light pattern are necessary. From this set-up, the 3D measurement of the scene can be carried out independently of one another both from a camera image pair (stereo set-up) and with a camera image and light pattern known thereto (camera/projector set-up). The 3D data are combined with one another (see Section 4 below) and thus together provide a denser 3D dataset due to the different perspectives. The two camera poses or the position of the camera and of the projector with respect to the scene must be different. The distance between two cameras or the camera and the projector is referred to in each case as the stereo base. This usually also applies for systems with more than two cameras, in that case pairings of two cameras each are build. The cameras and the projector are described geometrically by a pinhole camera model; the individual camera coordinate systems and the projector coordinate system are spanned in the respective focuses (=perspective projection center). The z-axes (=optical axis) of the coordinate systems are aligned such that they are oriented normal to the respective image planes. The position and orientation of the coordinate systems relative to one another has to be calibrated (=known) in order to be able to triangulate the 3D coordinates of the respective point in space in one of the two camera coordinate systems via individual corresponding regions in the respective stereo image pairs or in the camera image and projection pattern and via the known spatial position of the focal points. The optical aberrations (distortion of the image, pupil error) caused by the "real" optical lenses are compensated for, and the mathematical model is parameterized within the scope of the calibration procedure. The drawback of this method is that the compensation needed for the individual aberrations of each lens has to be measured separately for each lens used. However, since this calibration has to be made only once per lens this method is still advantageous over systems with constant calibration, since it preserves computational resources during measurement. The aberration compensation is applied to the raw two-dimensional image data. So for the purpose of 3D reconstruction the cameras are not only described by a pinhole camera model but also receive (idealized) measurement data as if taken by an idealized (pinhole) camera.

With a camera image pair and pairing of a known pattern and an image taken under a known angle combined the "densest" possible 3D reconstruction of the respective scene detail is enabled, since, in an ideal case, the coordinates of the respective point in space can be calculated for each corresponding point pair.

Based on the measurement principle, no additional light pattern source is necessary in the case of a stereo measurement method with two cameras. However, since the corresponding image points are to be extracted in the most stable and clear manner possible from almost non-textured tooth surfaces and the 3D reconstruction by means of triangulation using the camera/projector set-up has to be also implemented, in this case the projection of a (static) random (yet known) light pattern is used. This helps not only to overcome the disadvantageous texturing but also serves as illumination. Finding correspondences (identification of pointpairs) in stereo image pairs is in principle carried out via the evaluation of the neighborhood of each individual image point and is performed accurately to fractions of a pixel (subpixel accuracy). It also includes tilted correlation elements for equalization of the perspective distortion in the camera images ("slanted" correlation) and is calculated for a number of different resolution stages. The resultant measurement accuracy of the system is determined essentially by the quality of the calibration of the cameras relative to one another and by the calibration of the projector relative to the camera and by the reliability of the above-described correspondence finding.

The initial basis for the creation of a 3D model is an $S^3E$ depth image—it defines the origin of the model coordinate system (initiates the global coordinate system). In normal operation, the software provides the current $S^3E$ depth image and also a translation vector and the rotation matrix in order to fit this image into the predefined ray casting position. The position of the virtual raycaster camera moves together with the positioning of the hand-held tool and supplies the data of the overall model from the perspective of the previous $S^3E$ depth image as a virtual image (the virtual image being used in further calculations but can optionally also be displayed). The translation vector and the rotation matrix calculation (the registration) for a 3D measurement dataset recorded using the handset for "filling in" this 3D data to form an overall model (see Section 4) is performed using the ICP method (iterative closest point algorithm) [15].

3. ICP

The initial data from a registration are:
an $S^3E$ depth image from the current stereo camera pose,
the raycaster vertex map, and
the raycaster normal map from the previous stereo camera pose.

The following preprocessing steps are applied sequentially.

The $S^3E$ depth image from the current stereo camera pose and the raycaster vertex map plus the raycaster normal map from the previous stereo camera pose are reduced accordingly as required (subsample).

The 3D position of the image points (the $S^3E$ vertex map) and also the normal thereof ($S^3E$ normal map) are calculated from the respective current, reduced $S^3E$ depth image.

In addition, in each ICP step, the 3D points from the $S^3E$ vertex map are projected with the parameters of the raycaster camera onto a virtual camera image and are compared with the raycaster vertex map.

The input data for the ICP are as follows:
the current $S^3E$ vertex map from the view of the raycaster camera
the current $S^3E$ normal map from the view of the raycaster camera
the raycaster vertex map from the previous stereo camera pose
the raycaster normal map from the previous stereo camera pose Although in the used implementation an association between two points is defined not by its distance in 3D space but by back-projection of the 3D point from the $S^3E$ vertex map into the raycaster vertex map, thus it is decided on the basis of the 2D position in the depth image. The distance and the normal of the point located in the raycaster vertex map at the same location are only used in the second step for a plausibility check. This is necessary since all points in space along the viewing ray between the center of the camera and the image point are mapped on the image point.

The initial data of the ICP are as follows:
depth image from the current stereo camera pose,
translation vector (T) and rotation matrix (R)==>registration of the current $S^3E$ depth, image in the previous stereo camera pose and therefore in the overall model, and
registration quality (derived from the distances between points and the directions of the normal).

Additional initial data of the overall processing step are as follows:
normal map from the current stereo camera pose,
stereo matching quality, and
cliffmaps (see also 4.4).

3.1 Determining Camera Motion with Virtual Camera

Consecutively a short workflow how to determine the camera motion:
Obtain one or more 2D images (first image set) with physical camera from a position,
Reconstruct 3D information from (first) image set,
Obtain 3D information from virtual camera (e.g raycaster) out of global model. Said 3D information does not have to be equal in size with the 3D information reconstructed out of physical camera 2D images, Determine Correspondences (ICP), Determine camera motion (rotation matrix and translation vector), Update global model, Obtain again one or more 2D images (further image set) with physical camera from a new position, and Optionally restart at second step by reconstructing 3D information from the (further) image set.

Generally, 3D scanners are using either one or more physical cameras to obtain 2D data (generally one or more images) from one or more different perspectives and reconstruct 3D information (one or more individual frames or one or more segments) out of one or more obtained 2D images.

Said reconstructed 3D information is then used to register either i) one frame against a second frame or,
ii) one frame against a segment of frames or,
iii) one segment against another segment of frames or,
iv) one frame against a global model or,
v) one segment against a global model.

The used implementation, however, does not use physical camera based 3D information for the registration data, but uses as first part 3D information reconstructed from physical camera obtained 2D images and as second part 3D information obtained from a virtual camera by extracting said 3D information out of a global 3D model. The virtual camera itself does not obtain 2D images or 2D data, but works already on the basis of the global 3D model which comprises 3D information only. Said virtual camera does not have to reconstruct 3D information out of 2D information, but only to extract 3D data out of the global model from a perspective. Optionally the virtual camera may produce a 2.5D representation of the 3D data for further use, if needed. The 2.5D representation in this case can be a depth image (thus being "between" 2D and 3D).

4. TSDF

The truncated signed distance function (TSDF) indicates to the respective coordinates within the defined volume the distance to the next surface. The sign of the function value or distance value indicates whether this point is located in front of or behind the surface (as 'viewed' from the voxel in which the TSDF is noted), hence it is "signed". The actual surface is implicit and is located at the locations at which the function adopts the value zero. To determine the surface exactly, it is only necessary to know the exact distances merely close to the surface, and the function is thus cut off from a specific maximum distance and is interpreted as being "far away", hence it is "truncated".

During implementation, this function is described via values at the points of a uniformly distributed raster within a defined volume. Unless the surface is exactly located at the position of the raster point the TSDF value will never be exactly 0 (and if so it will simply be by chance and not reproducible). The actual surface can be found by interpolating in between the raster points and find out where the interpolation yields 0. The size of the volume has to be sufficiently large in order to contain the model to be recorded. Here, there must also be provision for a reserve, in case the model is not positioned optimally. If this volume is too small, the edge of the volume could be reached during the scanning process and the parts of the object outside this model structure region cannot be recorded. The number of raster points determines the required memory size during the model generation and also influences the speed of the system during the scanning process and during the evaluation. It goes without saying that these 'borders' are subject to evolving computational resources and can be estimated to grow in future.

In addition to the distance, there is at least a second entry for each volume element (voxel), and this is used to store additional information regarding the quality of the respective measured value.

The volume resolution is given from the volume size and the number of raster points, although either the volume can be reduced or the raster refined in order to achieve a higher resolution, depending on requirements.

4.1 TSDF Volume—Integration

In order to integrate new information from measurements/depth images into the model, the position of the scanner relative to the raster must also be known. Each element of the volume raster (voxel) is examined in order to establish whether it is affected by the new measurement and whether its value can be improved with the new information. If the voxel is in fact located in the viewing cone of the current measurement, it is associated with a viewing ray (position in the depth image).

As it is also described by Newcombe et al. [7] the TSDF update operates in a raster-oriented manner and is suitable for high-performance implementation on the GPU. The new depth data with established scanner position are integrated into the model by carrying out the following operations independently of one another for each raster point/voxel:

1. Establish voxel position from viewpoint of the camera.
2. Check as to whether and (if so) where (line, column, depth) the voxel is located in the depth image.
3. Integrate new voxel-to-surface distance information if there is a voxel in the depth image and the depth value is valid.

If this reference can be produced, associated depth value and values from other auxiliary images of the current measurement created before the volume integration can then be read and applied to distance and quality value of the voxel. Step 3 is not usually carried out for a large number of voxels, because these are located outside the viewing cone of the scanner and there is thus no new information for them.

For voxels within a viewing cone with valid depth value, the depth thereof relative to the camera is deducted from this depth value. The result is already the signed distance value at this position for the current measurement. If the distance is greater than the maximum cut-off, the voxel is located far outside in empty space (empty space update) according to the current measurement. If the value of the distance is smaller than the maximum, then it is located close to the measured surface (empty space update). Otherwise, the value is in the far negative range (less than (−maximum)) and the voxel is hidden and far behind the measured surface and should not be updated.

Depending on the distance, it is thus possible to distinguish between two essential different types of update. That which actually occurs with the voxel also differs however according to the state in which the voxel is located since the last update. Based on the combination of criteria from voxel status and new values, different strategies are selected for the present situation in order to improve the quality and accuracy of the distance value or at least not to impair this quality by conflicting data.

4.2 Voxel States

Figure 1:
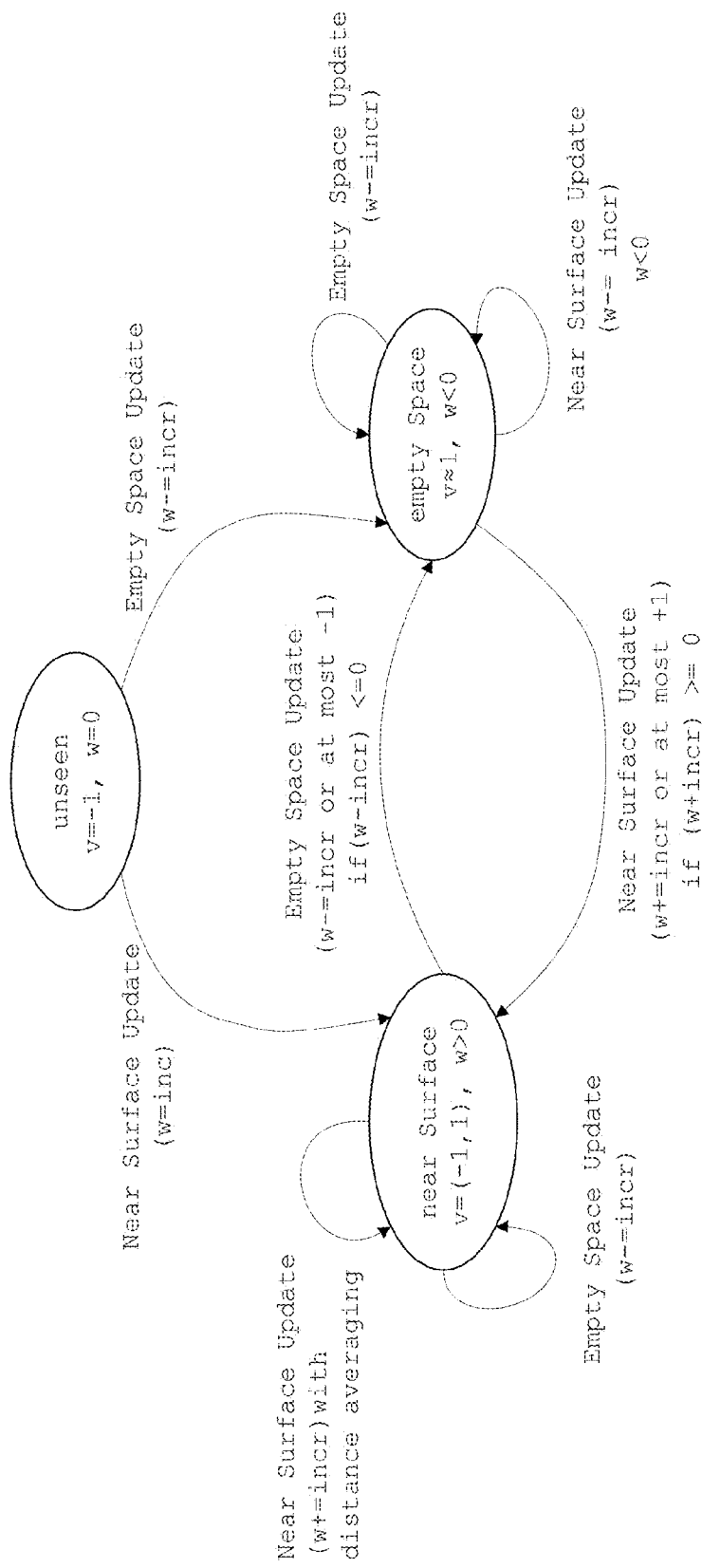
FIG. 1 shows how the voxel states are treated in the case of near surface and empty space updates and when they change.

A distinction can be made between three different states for each individual voxel (near surface, empty space and unknown) via the respective weighting value. The state chart in FIG. 1 shows how the voxel states are treated in the case of near surface and empty space updates and when they change.

Before the first measurement, all values in the grid are unknown (state: unknown) and, with the first update, immediately receive state, distance and weight from the respective update.

If a voxel is located close to a supposed surface (state: near surface) and a new update confirms this supposition, the new distance value is then established from voxel distance, measurement distance, voxel weight and weight of the measurement, and the voxel weight is increased. An empty space update contradicts the voxel value and state, and the weight is reduced. This can cause a state change to empty space, wherein the distance is also overwritten with the maximum value.

Vice versa, a voxel supposed as empty (state: empty space) will receive a weight further in the negative range. Near surface updates allow the value to rise as far as a state change with which the measured distance is adopted.

4.3 Intelligent Weighting

The accuracy of the measured values in the depth images is not completely constant. The accuracy to be expected reduces if the surface is not measured perpendicularly, but at a flat angle to the line of viewing. At problematic areas more measurements are necessary and good measurements are preferred in order to be able to generate a sufficiently accurate model.

In order to respond to this particular feature of the scanner and to be able to better evaluate the validity of an individual measurement for the model, the voxel weight is not only used as a simple counter (though in simpler implementations it can be just that). Depending on the estimation of the quality/accuracy, the current measurement is assigned a higher or a lower weight. The lower this value, the smaller is the influence on the voxel value in the current averaging and the less the weighting of the voxel is increased. Regions that were previously detected often, but only under poor conditions, were quickly improved by only a few good measurements.

The angle-weighting factor is given by the cosine of the angle between the depth image surface normal and the direction of the viewing ray. This decreases in value, the flatter the ray hits the surface (small angle of incidence).

The surface normals of the depth image are already generated in the ICP (registration) and are available for the TSDF update. The vectors already normalized are multiplied inversely (scalar product) by the viewing ray direction vectors (likewise normalized) in a vector image prepared before the start. This occurs before the TSDF update in a two-dimensional kernel and provides an image with the cosines for the respective depth values. This image is additionally smoothed by a box filter (9×9) before it is used in the TSDF update.

The intelligent weighting can be expanded in order to take into account additional quality criteria concerning the depth images (for example image quality from S3E or registration quality).

4.4 Cliff Distances

The Cliff approach by Frisken et al. [11] to close holes in the model was likewise implemented. Fundamentally, an area along the viewing rays is interpolated at relatively large stages between adjacent values in the depth image and generates matching distances for the grid in order to fill unknown regions. These interpolated distances are in turn overwritten immediately by measured values.

4.5 Brick Update

Together with the TSDF, a second, smaller raster is created. The number of raster points at the edges is lower by a fixed factor (for example 8 or 16). Each element represents a cube (brick) of voxels (for example 8×8×8 or 16×16×16) in the TSDF raster and indicates whether this cube could contain a surface. Should the brick contain only unsurveyed or empty space voxels, the brick is then labeled as empty. This information can be used to accelerate the surface calculation (raycaster, marching cubes) in order to be able to skip empty regions quickly without having to check each individual voxel, as it is explained by Sigg et al. [18] and Hadwiger et al. [5].

Figure 2:
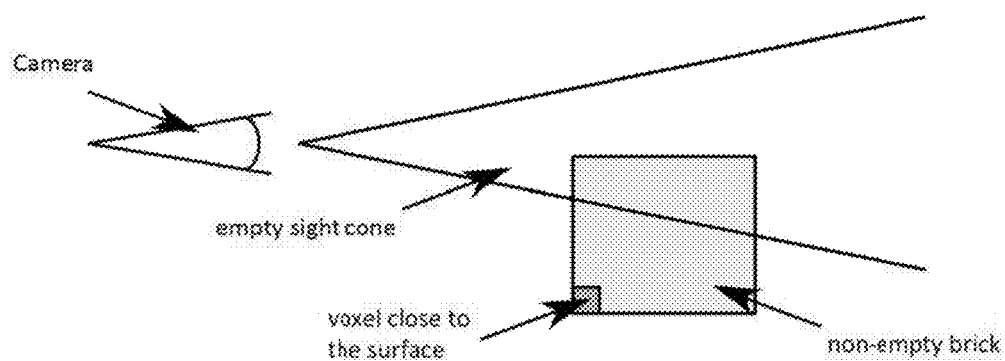
FIG. 2 shows a non-empty brick with empty viewing cone.

In order to save time and processing effort, only all bricks in the viewing cone are updated during the course of the TSDF update. For bricks outside this region, no change is to be expected because the associated voxels also do not change. Once all voxels in a brick within the viewing cone have been updated, it is examined as to whether one or more voxels are now close to a surface. If this is the case, it is recorded in the brick that it probably contains a surface. Hereto, all voxels of a brick have to be examined, even those that are indeed located outside the viewing cone but belong to a brick within the viewing cone (see FIG. 2).

The work groups are organized two-dimensionally, each processing a rectangular portion of one layer or slice of the three-dimensional dataset in parallel. Once the work items/threads have processed all their voxels in the brick, slice for slice (slices meaning groups of voxels, that are in regard of one axis on the same level of the brick, an n×n×n sized brick hence would have n slices each with a size of (1×)n×n), each that has found a voxel close to surface, sets a previously reset common memory point in the shared memory (_local) and waits until the entire work group is finished in order to obtain the new state for this brick.

Since all voxels of one slice ought to be processed parallel and this processing is preferably carried out by the GPU (see also section 7) it shall be understood that the brick size can be chosen even bigger with evolving GPU performance.

4.6 TSDF Gradient Condition

Figure 3:
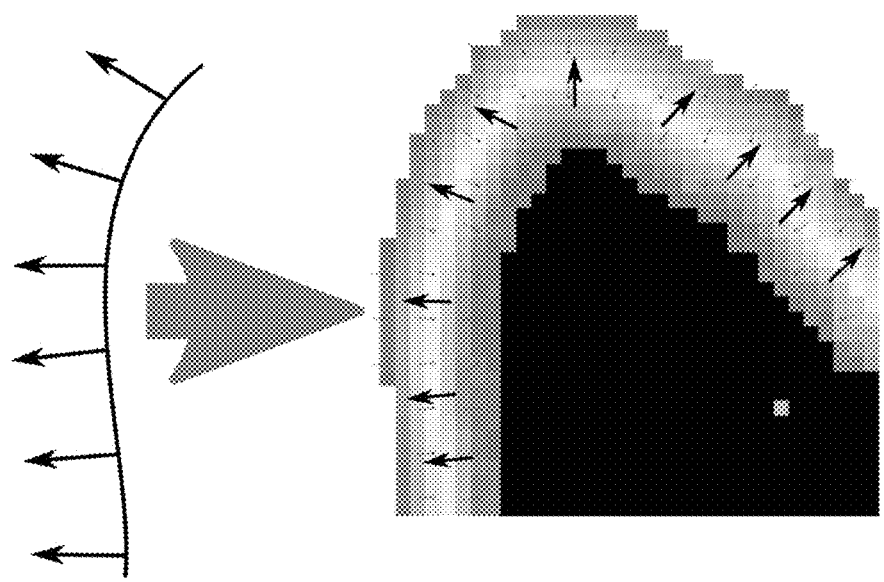
FIG. 3 shows surface normals from the depth image compared to the gradients of a TSDF detail.

The principle of the TSDF is that all voxel distances at a certain distance in front of and behind the currently measured surface are processed. However, there is thus always the risk of distorting another surface close in the background. Particularly at edges, "snowdrift-like" artifacts can be produced. In order to identify this situation, the orientation of the measured area in the depth image (surface normal) can be compared with the rough orientation of the distance function at the location of the voxel to be processed (see FIG. 3). The surface normals of the depth image are already provided by the ICP, but in coordinates with respect to the camera (Z-axis in camera viewing direction). For comparison with the TSDF gradients, a further vector image is created beforehand on the basis of the depth image normal and the camera pose, which contains the normal in global coordinates. In order to prevent surface normals being distorted by noise, they are combined linearly (weakly weighted, for example: 1:4) with the (inverse) viewing ray direction vectors before the coordinate transformation.

Three different situations arise from the comparison:

1. Update from the front: Surfaces in the depth image and model are oriented approximately identically; the new data match the voxel value.

2. Update from the rear: Surfaces in the depth image and model are oriented oppositely; the new data would distort another area here.

3. Ambiguous: The surfaces are inclined with respect to one another or have still been surveyed poorly/not at all.

Depending on which of the above mentioned situations has been identified, which of the above mentioned situations has been identified, the influence of the new measured value on the voxel value is now determined with various weighting functions. For rear and ambiguous cases, the quality value is reduced by the resultant weight, and conversely is increased in the case of a front update.

The weighting for updating from the front has the value "1" for good conformity and decreases linearly with the angle cosine up to the threshold value cos α=−δ as far as 0. There is less confidence in poorer conformities, and these are therefore afforded only a weak influence on the voxel value.

$$\cos\alpha\epsilon[-1\ldots-\delta]\to w_{front}=\frac{(-1)(\delta+\cos[\alpha])}{1-\delta} \quad \text{(Eq. 1)}$$

An update from the rear cannot generally be ruled out, since noise and outliers might generate voxels that fulfill this condition. If these voxel values wouldn't be updated ever again, they could turn into persistent artifacts. Instead, the new value is applied only to voxels that, according to their value, are less than $-\delta_{dist}$ behind the surface. The further is the voxel behind the surface and the greater is the value (voxel further away from the measured surface in the current depth image), the less is the confidence in the new value.

$$\cos\alpha\epsilon[\delta\ldots 1]\to w_{rear}=\max(0,\cos^{\frac{1}{2}}\alpha(-\delta_{dist}-d_{old})$$
$$(1-|d_{new}|^{\frac{1}{2}}) \quad \text{(Eq. 2)}$$

Figure 4:
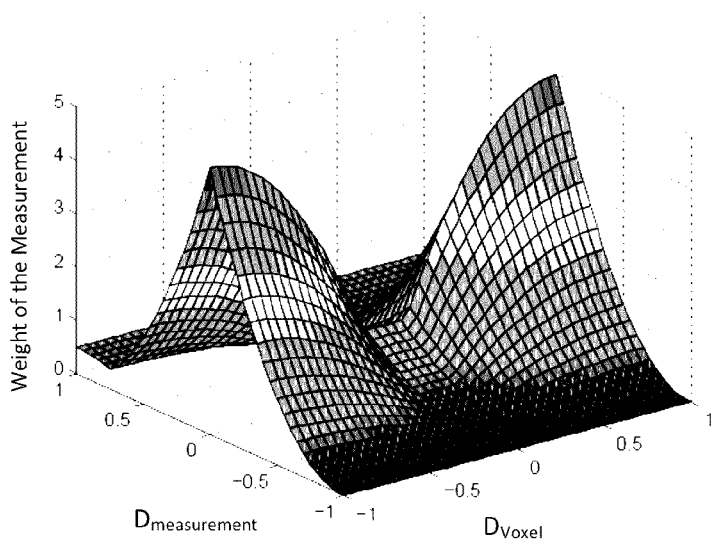
FIG. 4 shows a weighting function dependent on voxel value and new measurement for ambiguous cases.

In ambiguous cases, a weight that dampens snowdrift-like distortions without having a negative effect at other locations can only be established on the basis of the combination of voxel value and new measured value (see FIG. 4).

Figure 5:
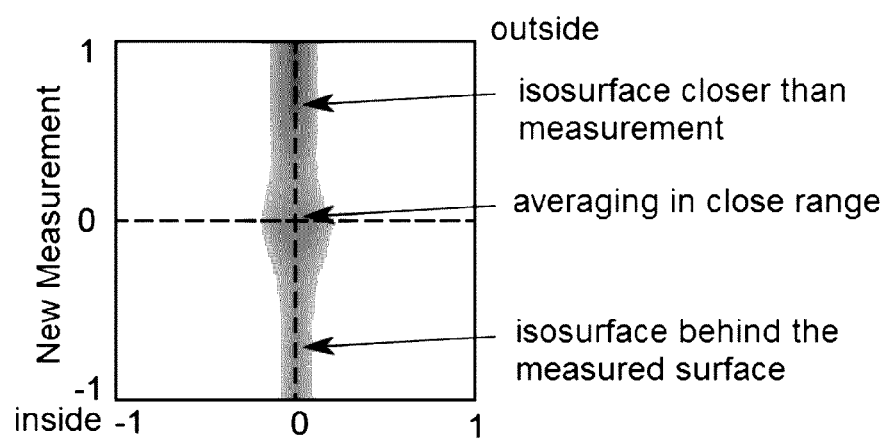
FIG. 5 shows interpretation of the regions of the weighting function.

The function $w=f(D_{old}, D_{new})$ is selected empirically such that it is symmetrical in the vicinity of the surface (both distances close to zero, see FIG. 5) and provides sufficiently high weights so as not to influence the averaging where possible.

If a voxel is believed to be very close to the surface ($D_{old}$ close to 0) according to previous measurements a new measurement yielding a large distance should not be trusted. Unless the surface has actually been moved inside the model area this larger value is likely to be an outlier, noise or telling the distance to a different surface on the back side. Therefor this condition will be treated by using a low weight for the update. However the weight should not be 0 in this situation either: the voxel might refer to a distance to an initial outlier or to the surface of a foreign body (for example tongue) that has been removed. If the update would be entirely banned, these invalid surfaces would persist in the model.

An averaging of surface voxels with measured values distanced further behind them (blue region in FIG. 5) can be produced as a result of isolated outliers and also as a result of foreign bodies removed in the meantime. It is thus sensible that even surfaces surveyed frequently can still be influenced by this.

Surface voxels that are located behind the area in the actual measurement (red region in FIG. 5) have to be treated rather more carefully, by contrast. Here, there is specifically a considerable risk that an area which is narrowly opposite will be influenced, particularly during updates at voxels already frequently measured.

4.7 Erasers

The discussed system is specifically intended for dental applications. Therefore, the scan object and its basic properties are given and can be used to specifically tailor the system to this kind of application for enhanced performance and usability. One such measure might for example be, to use rather short-wave illumination (wavelength below ~500 nm) since it is known that dental plaque is less penetrated by short-wave light which enhances scan accuracy.

The scanned (intentionally) object (jaw, teeth and so on) can be assumed to be static during the scanning process, if, during the scanning process, no teeth or dentures are inserted or removed. Undesired (unintentionally scanned) objects that the scanner sees, such as the tongue, cheeks, blood, saliva and foreign bodies are generally movable. This assumption can be used in order to considerably improve the performance, quality and comfort of the scanning process. Under the condition that the scan is started on a tooth, the jaw does not shift within the model. It is therefore impossible that tooth surfaces are present in regions at which the scanner is located or has been located.

During the TSDF update, regions that are located within the scanner volume (or any other specified volume, which can be larger or smaller than the scanner itself or even the same size, but moves along with the scanner/scannerhead) can be labeled permanently as empty (empty space) or the voxel update can be set to a certain value (e.g. minus 20). Undesired surfaces and artifacts can therefore be "rubbed out" by moving the scanner through them (for example: pushing aside a previously detected tongue). These regions can then be excluded permanently from the update. The processing effort is reduced and a subsequent emergence of new artifacts in this region can also be prevented.

This "eraser" could likewise be implemented in a raster-oriented manner and uses the camera coordinates of the voxel that are determined during the TSDF update. The coordinates are examined with regard to whether they lie within a simplified model of the scanner head. If this is the case, the considered voxel is characterized permanently as "far away" without further examination, and areas generated previously in error are deleted.

Figure 6A:
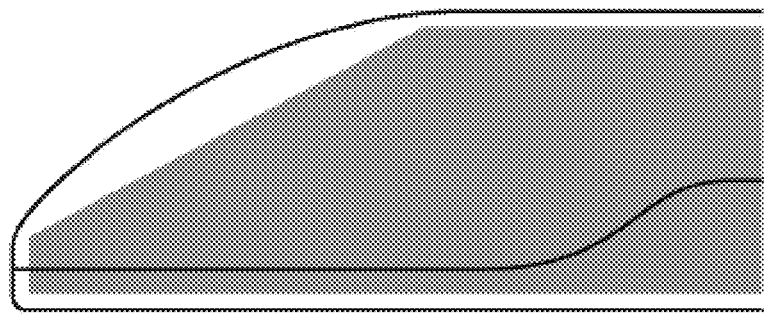
FIG. 6a shows a simplified eraser volume within the scanner head.
Figure 6B:
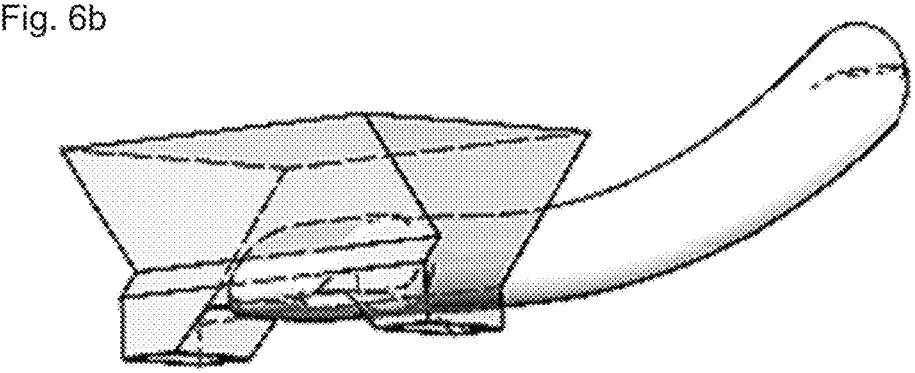
FIG. 6b shows a complex eraser volume, larger than the scanner head.

In the ideal case, the modeled volume is identical to the volume of the scanner, but in practice it should be slightly smaller (for example: 5%) but can also be significantly larger at areas that are not likely to ever collide with real teeth (see FIG. 6b). By simplifying the surface, the volume may also easily be significantly smaller in some places compared to the actual dimensions (see FIG. 6a). If the modeled volume is exactly the same size or larger, correctly measured tooth surfaces could also be deleted in scanner operation as a result of registration fluctuations when the scanner rests there.

On the other hand there might be circumstances where it could be useful to expand the eraser volume beyond the outline of the scanner to ban update in regions that would only contain undesired surface fragments anyway. If the specific intent is to scan a half jaw anything behind the scanner could be erased quite generously without corrupting the desired model. If the scanner is known to be located in a occlusal position, the eraser could expand to the sides to remove or prevent fragments from tongue and cheek.

In the intraoral environment two erasers can be overlaid. Both erasers with a different volume whereby one is preferred to be smaller than the other, hence, the smaller one is a part of the larger one. Both erasers can be conFigured to work in different modes. For example can one eraser set the voxel updates to minus 20 and the other eraser can be conFigured to set the voxel updates to e.g. minus 30000 which means that the areas are removed permanently. The voxel areas with the minus 20 weighting can be visualized again after more than 20 updates without having the eraser moving into those areas.

5. Marching Cubes

With the intraoral scanner, the recorded surface is stored as an implicit area in the form of a signed distance function $F(x,y,z)$. For points $(x,y,z)$ on the actual surface, $F(x,y,z)=0$ applies; for points in front of or behind the surface, $F(x,y,z)$ is a measure for the positive or negative distance of the points from the true surface. In the present case, the distance function $F(x,y,z)$ is represented by the specification of its values on a discrete grid (what is known as a voxel grid), that is to say the values $F(i,j,k)$ where $i,j,k=0, \ldots, m$ are known. At the discrete locations of the voxel grid, the implicit distance function $F(x,y,z)$ will generally not be identical to zero. A method for extracting the isosurface from the discrete voxel grid at isovalue zero is thus required.

Figure 7:
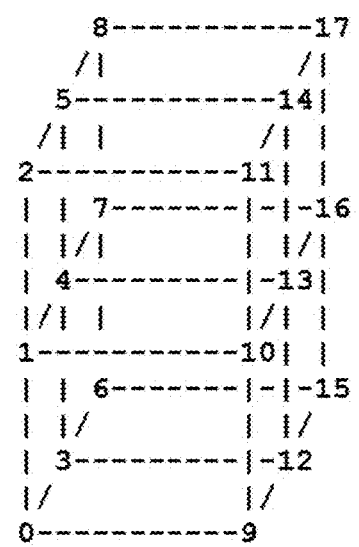
FIG. 7 shows four cubes adjoining one another.

Alongside "Marching Tetrahedrons" (see [14]) "Marching Cubes" (see [20]) is the standard method for extraction of isosurfaces from volumetric datasets, In this case, the voxel grid, which constitutes an implicit representation of the object surface, is initially broken down into cubes (build by eight adjacent voxels, which are forming the cube's corners). It is then determined for each cube how the actual surface passes through it and the corresponding surface piece is represented by a number of triangles (usually one to five). The way in which the object surface runs through a cube is determined here on the basis of the values of the voxel grid at the eight corners of the cube. In the case of the presented intraoral scanner, the voxel grid stores not only the actual distance values, but also weights, which are a measure for the quality of each of said distance values. These weights have to be taken into consideration when determining the triangles per cube. If the surface runs through all cubes of the voxel grid, all triangles produced therefore represent the geometry of the surface of the object. The present optimization of the Marching Cubes algorithm primarily concerns the clever formulation of various code constructs. Here, it was attempted to access the memory as linearly as possible and to take maximum advantage of the caching of the CPU. One aspect here is that not just one cube is read from the memory, but four (see FIG. 7).

The data structure used was selected such that as few points as possible have to be read more than once. This procedure also means that many related operations are arranged "close" to one another, which assists the pipelining of the CPU but also the compiler in the event of a possible "vectorization" of the code.

6. Ray Casting

Ray tracing is generally complicated. A simplification by what is known as ray casting is therefore used. That is, only primary rays are traced (occlusion calculation). However, there is no secondary ray tracing, such as no shadows, reflections, highlights or the like. Ray casting allows a calculation of intersection, normal vector calculation and "shading" to be carried out.

6.1 Calculation of Intersection

The area is given implicitly by the distance function: $tsdf=F(x,y,z)$.

The level surface (isosurface) with $F(x,y,z)=constant=0$ is then sought. This gives an implicit function $F(x,y,z)=0$. (The explicit representation for this would be: $z=f(x,y)$).

Figure 8:
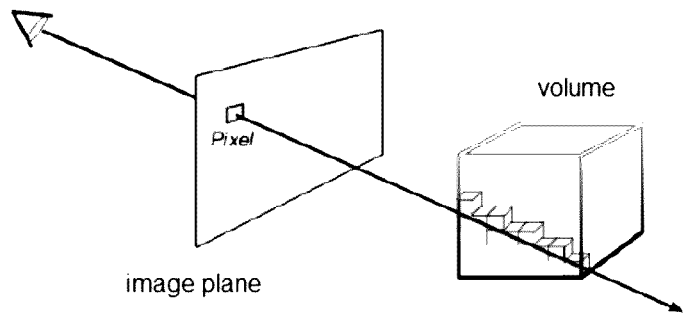
FIG. 8 shows ray casting.
Figure 9:
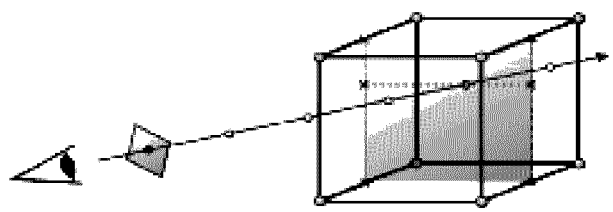
FIG. 9 shows calculation of intersection by ray casting.

The implicit area is extracted by means of ray casting. In doing so, a ray is sent through each pixel from the eye of the viewer (center of the camera projection) through the volume. Along the ray, the distance values stored in the relevant voxels are tested for a change of sign (zero crossing). Thereby, when the ray passes through the voxel, a weighted mean value is established from the stored scalar values of the 8 adjacent voxels by means of trilinear interpolation. See FIG. 8 and FIG. 9.

Figure 10:
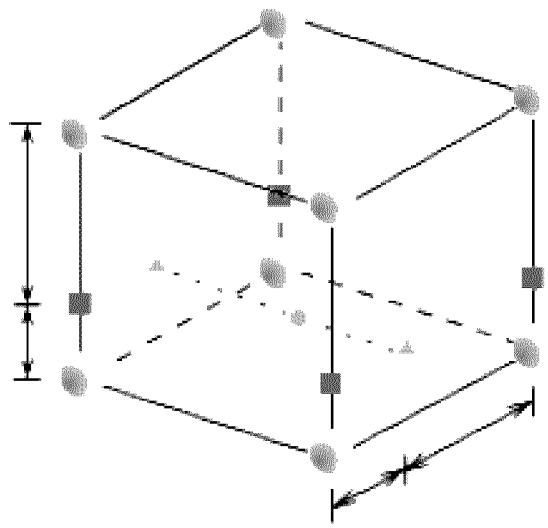
FIG. 10 shows trilinear Interpolation.

The coordinates of the intersection of the ray with the isosurface are then determined in turn by interpolation between the two scalar values along the ray. See FIG. 10.

Since the area can only be within the voxel grid (bounding box), it must first be established whether the ray actually contacts the bounding box at all. If so, the point of entry and point of exit of the ray with the bounding box are calculated. The intersection test clearly only takes place within these two points. To this end, the positional relationships of a straight line and a plane are first considered in greater detail.

6.1.1 Positional Relationships Between a Straight Line and a Plane in $R^3$ A straight line $g: \vec{x}=\vec{G}+t\cdot\vec{V}$ and a plane $\epsilon \vec{X}=\vec{E}+r\cdot\vec{U}+s\cdot\vec{W}$ can be arranged relative to one another as follows:

g intersects $\epsilon$,
g is oriented parallel to $\epsilon$,
g lies in $\epsilon$.

Let the straight line g and the plane $\epsilon$ then be as follows:

$$g: \begin{pmatrix} x \\ y \\ z \end{pmatrix} = \begin{pmatrix} g_1 \\ g_2 \\ g_3 \end{pmatrix} + t \cdot \begin{pmatrix} v_1 \\ v_2 \\ v_3 \end{pmatrix} \quad \text{(Eq. 3)}$$

$$\epsilon: \begin{pmatrix} x \\ y \\ z \end{pmatrix} = \begin{pmatrix} e_1 \\ e_2 \\ e_3 \end{pmatrix} + r \cdot \begin{pmatrix} u_1 \\ u_2 \\ u_3 \end{pmatrix} + s \cdot \begin{pmatrix} w_1 \\ w_2 \\ w_3 \end{pmatrix} \quad \text{(Eq. 4)}$$

A plane that is parallel to the ZX plane will now be observed, considering this the parametric representation of the plane can be formulated as follows:

$$\begin{pmatrix} x \\ y \\ z \end{pmatrix} = \begin{pmatrix} e_1 \\ e_2 \\ e_3 \end{pmatrix} + r \cdot \begin{pmatrix} 1 \\ 0 \\ 0 \end{pmatrix} + s \cdot \begin{pmatrix} 0 \\ 0 \\ 1 \end{pmatrix} \quad \text{(Eq. 5)}$$

If the straight line g intersects this plane, the following three equations are obtained:

$$g_1 + t \cdot v_1 = e_1 + r$$

$$g_2 + t \cdot v_2 = e_2$$

$$g_2 + t \cdot v_2 = e_2 + s \quad \text{(Eq. 6)}$$

The second equation gives the following for the parameter t in the equation of the line, mentioned at the beginning of this subchapter:

$$t = \frac{c_2 - g_2}{v_2} \quad \text{(Eq. 7)}$$

If then $v=0$ and $e_z-g_z\neq 0$, the straight line is then oriented parallel to the XZ plane, since, in the straight-line equation, the Y component $v_z$ of the direction vector is equal to zero.

If $v_2=0$ and $e_z-g_z\neq 0$, the straight line then lies in the XZ plane. (Since $v_z$ is equal to zero, the straight line must initially be parallel to the XY plane. Because the Y components $e_2$ and $g_2$ of the points on the straight line and plane are of equal size, the straight line point must therefore lie in the plane).

All other cases result in a single intersection of the straight line and the plane.

Similar results are obtained for the planes that are parallel to the XY plane or to the ZY plane.

The parametric representation $$\begin{pmatrix} x \\ y \\ z \end{pmatrix} = \begin{pmatrix} e_1 \\ e_2 \\ e_3 \end{pmatrix} + r \cdot \begin{pmatrix} 1 \\ 0 \\ 0 \end{pmatrix} + s \cdot \begin{pmatrix} 0 \\ 1 \\ 0 \end{pmatrix} \quad \text{(Eq. 8)}$$

is obtained for the intersection g with a plane parallel to the XY plane and, from this, the parameter $$t = \frac{e_3 - g_3}{v_3} \quad \text{(Eq. 9)}$$

is obtained for the intersection with the straight line.

If now $v_2=0$ and $e_2-g_2\neq 0$, the straight line then lies parallel to the XY plane.

If now $v_2=0$ and $e_2-g_2=0$, the straight line then lies in the XY plane.

All other cases give a clear intersection of the straight line and the plane.

The parametric representation $$\begin{pmatrix} x \\ y \\ z \end{pmatrix} = \begin{pmatrix} e_1 \\ e_2 \\ e_3 \end{pmatrix} + r \cdot \begin{pmatrix} 0 \\ 1 \\ 0 \end{pmatrix} + s \cdot \begin{pmatrix} 0 \\ 0 \\ 1 \end{pmatrix} \quad \text{(Eq. 10)}$$

is obtained for the intersection g with a plane parallel to the ZY plane and, from this, the parameter $$t = \frac{e_1 - g_1}{v_1} \quad \text{(Eq. 11)}$$

is obtained for the intersection with the straight line.

If now $v_1=0$ and $e_1-g_1\neq 0$, the straight line then lies parallel to the YZ plane.

If now $v_1=0$ and $e_1-g_1=0$, the straight line then lies in the YZ plane.

All other cases give a single intersection of the straight line and the plane.

6.1.2 Trilinear Interpolation

The data grid that describes the isosurface is discrete. It is therefore very likely that sampling points along the viewing ray do not fall exactly on data points in the grid, but lie somewhere in between.

For this reason, the missing values of the function are interpolated from those present. Trilinear interpolation is used for this purpose. Here, the scalar values of the eight adjacent voxels of a sampling point are weighted on the basis of their three coordinate distances from the sampling point (see FIGS. 8, 9 and 11).

For improved comprehension, linear interpolation will be explained first.

Linear Interpolation

The simplest interpolation formula is that of linear interpolation. The equation of the straight line between the two adjacent points is easily determined. The equation is given on the basis of the similarity of the triangles in the considered interpolation interval.

$$\frac{f(x) - f(x_0)}{x - x_0} = \frac{f(x_1) - f(x_0)}{x_1 - x_0} \quad \text{(Eq. 12)}$$

wherein $x_0 \leq x \leq x_1$.

After rearrangement:

$$f(x) = \frac{x - x_0}{x_1 - x_0}(f(x_1) - f(x_0)) + f(x_0) \quad \text{(Eq. 13)}$$

If the following substitution is then made:

$$u := \frac{x - x_0}{x_1 - x_0}, \quad \text{(Eq. 14)}$$

then the interpolation interval would be normalized to [0, 1]. In other words, $0 \leq u \leq 1$.

In addition:

$$1 - u = 1 - \frac{x - x_0}{x_1 - x_0} = \frac{x_1 - x_0 - x + x_0}{x_1 - x_0} = \frac{x_1 - x}{x_1 - x_0} \quad \text{(Eq. 15)}$$

With $f_1 := f(x_1)$, $f_0 := f(x_0)$, the following is then given:

$$f(u) = u \cdot (f_1 - f_0) + f_0 \quad \text{(Eq. 16)}$$

or $$f(u) = u f_1 + (1-u) f_0, 0 \leq u \leq 1 \quad \text{(Eq. 17)}$$

If a zero point for example is then sought in this interval, that is to say $f(u)=0$, then the following equation is obtained:

$$0 = u \cdot (f_1 - f_0) + f_0 \quad \text{(Eq. 18)}$$

and therefore $$u = -\frac{f_0}{f_1 - f_0} \quad \text{(Eq. 19)}$$

Figure 12:
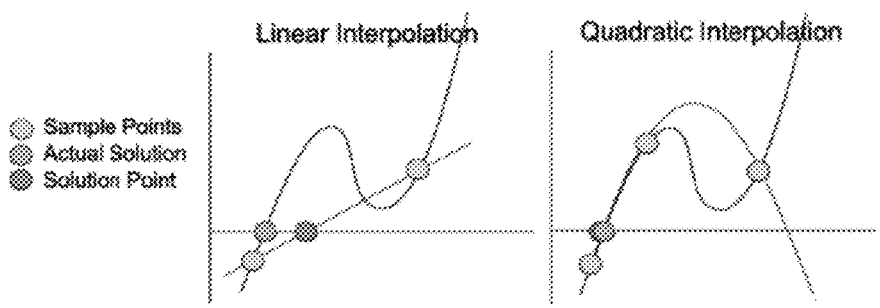
FIG. 12 shows linear interpolation vs. quadratic interpolation.

For a comparison between linear and quadratic interpolation see FIG. 12.

Trilinear Interpolation

Figure 11:
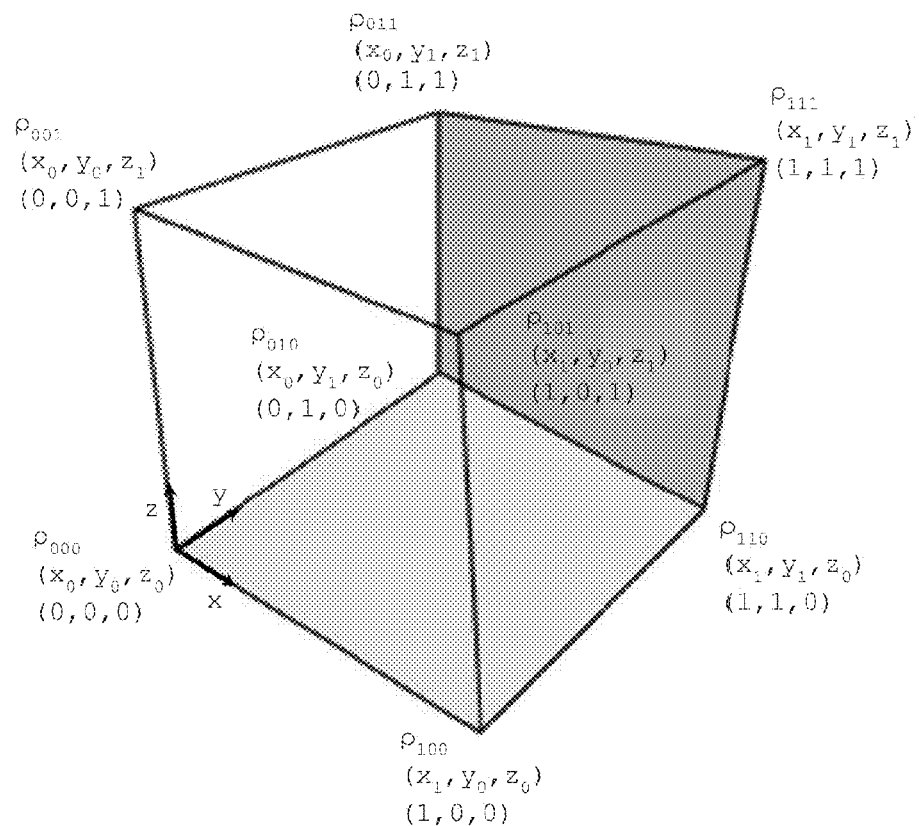
FIG. 11 shows trilinear interpolation.

Trilinear interpolation with the interpolation weights u, v and w corresponds in FIG. 11 in each case to a linear interpolation along the x axis, the y axis and the z axis. It is thus a generalization of linear interpolation in three dimensions. The interpolation formula is obtained similarly to formula (17).

The data value at a sampling point within a voxel, obtained by trilinear interpolation of the 8 corner values $\rho_{00_0} \cdots \rho_{11_1}$ $\rho_{00_0} = F(i,j,k)$ $\rho_{10_0} = F(i+1,j,k)$ $\rho_{01_0} = F(i,j+1,k)$ $\rho_{11_0} = F(i+1,j+1,k)$ $\rho_{00_1} = F(i,j,k+1)$ $\rho_{10_1} = F(i+1,j,k+1)$ $\rho_{01_1} = F(i,k+1,k+1)$ $\rho_{11_1} = F(i+1,j+1,k+1)$ (Eq. 20)

with the indices i,j,k, (for the left lower front corner of the voxel to be interpolated), is given by the three linear interpolation weights u, v, w∈[0,1]:

$$u = \frac{x - x_0}{x_1 - x_0} \text{ or } 1 - u = \frac{x_1 - x}{x_1 - x_0}$$
$$v = \frac{y - y_0}{y_1 - y_0} \text{ or } 1 - v = \frac{y_1 - y}{y_1 - y_0}$$
$$w = \frac{z - z_0}{z_1 - z_0} \text{ or } 1 - w = \frac{z_1 - z}{z_1 - z_0}$$ (Eq. 21)

These weights can also be calculated with the aid of the floor function. This representation is used for example in [13]:

$u = x - \lfloor x \rfloor,$ $v = y - \lfloor y \rfloor,$ $w = z - \lfloor z \rfloor,$ (Eq. 22)

And this gives the interpolated function value as:

$\rho(u,v,w) = (1-u)(1-v)\rho_{00_0} +$ $(1-u)(1-v)(w)\rho_{00_1} +$ $(1-u)(v)(1-w)\rho_{00_1} +$ $(u)(1-v)(w)(1-w)\rho_{10_0} +$ $(u)(1-v)(w)\rho_{00_1} +$ $(1-u)(v)(w)\rho_{00_1} +$ $(u)(v)(1-w)\rho_{11_0} +$ $(u)(v)(w)\rho_{11_1}$ (Eq. 23)

Equation 23 is the three-dimensional counterpart to Equation 17 for one-dimensional linear interpolation. If is defined that $u_0 := (1-u)$ and $u_1 := u$, and analogously for $v_0, v_1, w_0, w_1,$ the interpolated function value can then also be represented by the compact equation $$\rho = \sum_{i,j,k=0,1} u_i v_j w_k \rho_{ijk}$$ (Eq. 24)

In this regard, see the paper concerning ray tracing by S. Parker [8].

Calculation of the Intersection by Means of Interpolation

In the intersection test, a sign change in the previously trilinearly interpolated function value between two successive sampling points along the line of sight is tested for.

If $\vec{A}$ and $\vec{B}$ are now two points with different signs of the function value, the following parametric representation is valid for a straight line g, which passes through $\vec{A}$ and $\vec{B}$ $g: \vec{X} = \vec{A} + t \cdot (\vec{B} - \vec{A}), 0 \le t \le 1$ (Eq. 25)

For t=0, point $\vec{A}$ is obtained, and for t=1, point $\vec{B}$ is obtained. For all other values of t between 0 and 1, points along the ray that lie between $\vec{A}$ and $\vec{B}$ are obtained. If the scalar value at the resampled point $\vec{A}$ is denoted by $F_A$ and the scalar value at point $\vec{B}$ is denoted by $F_B$, linear interpolation can thus be carried out between these two function values according to equation 17 as follows:

$f(t) = t \cdot F_B + (1-t) \cdot F_A$ (Eq. 26)

If the point $\vec{X}$ on the isosurface is then sought, for which $F(\vec{X}) = f(t) = 0$ must indeed apply, then the condition $$t = -\frac{F_A}{F_B - F_A}$$ (Eq. 27)

is obtained, as already found in equation 19. If the t now calculated is substituted into equation 25, the coordinates for the intersection of the ray with the isosurface are then known.

A slightly more general approach is now considered:

Taking $P_{\overrightarrow{start}}$ now as the starting point of the ray and $\vec{V}$ its normalized direction vector, an arbitrary point $\vec{A}$ over the ray can then be represented as follows by means of the equation of a line with a suitable parameter $t_A$:

$\vec{A} = P_{\overrightarrow{start}} + t_A \cdot \vec{V}$ (Eq. 28)

For a further point $\vec{B}$, the following then applies $\vec{B} = P_{\overrightarrow{start}} + t_B \cdot \vec{V}$ (Eq. 29)

Taking the difference of the two above equations, this gives $\vec{B} - \vec{A} = (t_B - t_A) \cdot \vec{V}$ (Eq. 30)

If $\Delta t := t_B - t_A$, then $\vec{B} - \vec{A} = \Delta t \cdot \vec{V}$ and the ray can be represented as follows with the aid of equation 25:

$\vec{X} = \vec{A} + t \cdot (\vec{B} - \vec{A}) = P_{\overrightarrow{start}} + t_A \cdot \vec{V} + t \cdot \Delta t \cdot \vec{V} = P_{\overrightarrow{start}} + (t_A + t \cdot \Delta t) \cdot \vec{V}, 0 \le t \le 1$ (Eq. 31)

If $t^* := t_A + t \cdot \Delta t$, the following is thus obtained according to equation 27

$$t^* = t_A + t \cdot \Delta t = t_A + \left(-\frac{F_A}{F_B - F_A}\right) \cdot \Delta t$$ (Eq. 32)

and the following is therefore given for the value of the parameter at the interpolated intersection $$t^* = t_A - \frac{\Delta t \cdot F_A}{F_B - F_A} \quad \text{(Eq. 33)}$$

This representation is advantageous if scanning is carried out iteratively with constant $\Delta t$ along the ray. It corresponds exactly to the formula 15, specified in the Kinect paper [7] under section 3.4.

The intersection is obtained with $$\vec{X} = \vec{P_{start}} + t^* \cdot \vec{V} \quad \text{(Eq. 34)}$$

6.1.3 Refined Interpolation Methods

There are a number of refinement methods for more accurate determination of the intersection.

Bisection Method

A. Neubauer et al. [3] presented an iterative linear interpolation. It is based on the principle of nested intervals known from one-dimensional analysis. If the scalar value according to trilinear interpolation is assumed to be positive at point $\vec{A}$ and negative at point $\vec{B}$, the intersection is then calculated by means of linear interpolation of the intersection. Depending on whether the scalar value to be newly calculated via trilinear interpolation is negative or positive at this intersection, the sub-interval where a sign change takes place is taken and then the same method is applied again. This provides a very good approximation value for the intersection after just a few iterations. In this regard, see [12], [4] and [3]. In [12] and [4] some pseudo code can also be found.

Inverse Quadratic Interpolation

N. Tatarchuck et al. [6] propose in their paper a further possibility for refining the interpolation. This is inverse quadratic interpolation.

For the data $\vec{x_0}, \vec{x_1}, \vec{x_2}, f_i 2$), the approximation then has the form $$\vec{x_*} \approx \frac{f_1 f_2}{(f_1 - f_0)(f_2 - f_0)} \vec{x_0} + \frac{f_0 f_2}{(f_0 - f_1)(f_2 - f_1)} \vec{x_1} + \frac{f_0 f_1}{(f_0 - f_2)(f_1 - f_2)} \vec{x_2}. \quad \text{(Eq. 35)}$$

If one starts with two points $\vec{A}$ and $\vec{B}$ at which the scalar function $f$ changes its sign, inverse interpolation can thus be combined very effectively with the bisection method. As a third point, the point obtained from simple linear interpolation according to equation (34) can be used. On this point, see the method by R. Brent [2] and W. Press et al. [9].

Cubic Interpolation

For a more exact determination of the intersection, S. Parker et al. [8] specify formulas for the coefficients of a cubic equation with regard to the parameter t of the ray. The zero points of this equation are then determined using Cardano's method for cubic equations. However this method is computationally very intensive.

6.1.4 Acceleration Methods

When calculating the intersection, so as not to have to pass though an unnecessary number of voxels along the ray that contain no component for surface determination, various efficient acceleration methods are proposed.

Mentioned here are:

Hierarchical Structure of the Volex Volume by means of Octree or KD tree

For example see [19] and [10].

and

Empty Space Skipping

This method is easily applicable and efficient. The voxel volume is divided into individual blocks (bricks) of equal size (for example 8 voxels in each direction). The maximum value and minimum value of the scalar value (TSDF value) of each brick must be known. As the bricks are passed through along the ray, the brick is then discarded if the maximum value and minimum value of the brick each have the same sign. In this regard see also [5] and [18].

A further variant of this method is presented by Newcombe et al. [7] in Chapter 3.4. In this case, the ray is continued by a length that is smaller than the truncation value (MIN TRUNCATION). Provided the TSDF value is equal to the positive truncation value (in the case of normalized truncation that is to say equal to 1) along the course of the ray, the voxel can be skipped.

6.2 Normal Vector Calculation

The sought isosurface is given implicitly by the distance function $$tsdf = F(x,y,z) \quad \text{(Eq. 36)}$$

The gradient of the distance function is defined as:

$$\nabla F(x, y, z) = \begin{pmatrix} F(x+1, y, z) - F(x-1, y, z) \\ F(x, y+1, z) - F(x, y-1, z) \\ F(x, y, z+1) - F(x, y, z-1) \end{pmatrix} \quad \text{(Eq. 38)}$$

$$x, y, z \in N$$

For implicit functions, the following is true:

The gradient is also the normal vector at the level surface (isosurface) $F(x,y,z)=0$.

For numerical purposes, the gradient can be calculated only at discrete points. Fo this purpose, the so-called "central difference" is used. From a geometric point of view, it is the three-dimensional analogon to the one-dimensional secant method, in which the slope of the curve in a point is approximated by the slope of the secant between two adjacent points.

$$\nabla F = \left( \frac{\partial F}{\partial x}, \frac{\partial F}{\partial y}, \frac{\partial F}{\partial 2} \right) \quad \text{(Eq. 37)}$$

This gradient is then normalized and thus gives a unit normal vector $\vec{n}$ on the surface.

$$n = \frac{\nabla F}{\|\vec{n}\|} \quad \text{(Eq. 39)}$$

In the publication by S. Parker et al. [8], a further possibility for numerically determining the gradient is presented (in the chapter concerning trilinear interpolation of the referenced paper [8]).

6.3 Shading

Shading by means of ray tracing is generally complicated. The desired illumination method to be used is therefore of great importance.

Ray casting:
Occluded surfaces—local illumination method
Recursive ray tracing:
Reflection, reffraction, surface light as a point—local illumination model
Photon mapping:
Correct illumination—global illumination model
Phong Illumination Model In the "Phong model", which is a local illumination model, the total illumination is modeled as the sum of three individual components. The light reflection is described as a combination of ambient, ideally diffuse and ideally specular reflection. In addition, the light source is assumed to be a point light source. Furthermore, it is understood that the light source is infinitely far away, that is to say all light rays contact the surface from the same direction, that is to say they are parallel to one another. See also [1].

$$I_{out} = I_{ambient} + I_{diffuse} + I_{specular} \tag{Eq. 40}$$

The individual components are then defined as follows:
Ambient Component of the Reflected Light The ambient component of the reflected light is independent of the angle of incidence of the light ray of the point light source and of the viewing angle of the observer of a scene. It is dependent on the ambient light, which is constant for all points on all surfaces, and on an empirically determined reflection factor (material constant).

$$I_{ambient} = k_{ambient} \cdot I_a \tag{Eq. 41}$$

where
$I_a$ ... is the intensity of the ambient light
$k_{ambient}$ ... is a material constant
Diffuse Component of the Reflected Light With diffuse reflection, the light is reflected in all directions independently of the viewpoint of the observer (Lambert's cosine law). The intensity of the reflected light of the point light source is still dependent on the angle of incidence, since the illumination intensity of the surface changes with the angle of incidence. The light intensity of the diffuse components is thus dependent on the angle of incidence of the light ray of the point light source and on an empirically determined reflection factor (material constant), but is independent of the viewing angle of the observer of the scene.

$$I_{diffuse} = k_{diffuse} \cdot \cos\phi \cdot I_{in} \tag{Eq. 42}$$

where
$I_{in}$ ... is the intensity of the incident light ray of the point light source
$k_{diffuse}$ ... is an empirically determined reflection factor for the diffuse component
$\phi$ ... is the angle between the normal vector $\vec{n}$ of the surface and unit vector in the direction of the incident light ray $\vec{l}$.

The following is also true for the angle $\phi$:

$$\cos\varphi = \frac{\langle \vec{n}, \vec{l} \rangle}{\|\vec{n}\|\|\vec{l}\|} \tag{Eq. 43}$$

Specular Component of the Reflected Light

In specular reflection the light is reflected within a certain proximity of the ideal reflection direction. The intensity of the reflected light is dependent on the angle of incidence of the light ray of the point light source, on an empirically determined reflection factor (material constant), and on the nature of the surface and on the viewing angle of the observer of the scene.

$$I_{specular} = k_{specular} \cdot \cos^s\theta \cdot I_{in} \tag{Eq. 44}$$

where
$I_{in}$ ... is the intensity of the incident light ray of the point light source
$k_{diffuse}$ ... is an empirically determined reflection factor for the diffuse component
$\theta$ ... is the angle between the reflection direction of the emergent light ray $\vec{r}$ and the viewing direction of the observer $\vec{v}$.
s ... is a constant exponent (shininess factor) for describing the nature of the surface (rough less than 32, smooth greater than 32, n=∞ would be a perfect mirror).

For a large s, more light is reflected (dotted) in the ideal direction, and with smaller S more light is scattered. The specular effect is thus highly dependent on the shininess factor s.

The following is also true for the angle $\theta$:

$$\cos\varphi = \frac{\langle \vec{r}, \vec{v} \rangle}{\|\vec{r}\|\|\vec{v}\|} \tag{Eq. 45}$$

Complete Formula of the Phong Model
The complete formula is therefore $$I_{out} = k_{ambient} \cdot I_a + (k_{diffuse} \cdot \cos\phi + k_{specular} \cdot \cos^s\theta) \cdot I_{in} \tag{Eq. 46}$$

For the factors occurring here, a convex combination is used. (In real spaces, a linear combination is called a convex combination if all coefficients originate from the unit interval [0,1] and their values sum to 1).

$$k_{ambient} + k_{diffuse} + k_{specular} = 1 \tag{Eq. 47}$$

Simplified Local Illumination Model

A simplification is obtained if, in the Phong model, only the diffuse component is used. In other words, no ambient component (ambient light) and no reflective component (specular component) are used. Only the ray (primary ray) is therefore traced until it impinges on the surface (no secondary ray tracing such as shadow sensors, reflections, etc.).

Our illumination model therefore reduces to Lambert's cosine law.

Equation 46 reduces to $$I_{out} = k_{diffuse} \cdot \cos\phi \cdot I_{in} \tag{Eq. 48}$$

This law is then used to determine the grey value of the pixel.

Since ambient and specular portions are omitted, the factor $k_{diffuse} = 1$ can be set according to formula (47).

If the color consists only of grey values for example, the color values of all three color channels in the RGB color space then have to be of equal size. With 8-bit color depth per color channel, this would be (255, 255, 255) for the color white.

In accordance with this simplified illumination model, if RGB is the color value, the pixel color, that is to say the grey value, is thus $$RGB_{Lambert} = RGB_{white}\cos\varphi - RGB_{white}\frac{\langle \vec{n}, \vec{l} \rangle}{\|\vec{n}\|\|\vec{l}\|} \tag{Eq. 49}$$

Figure 13:
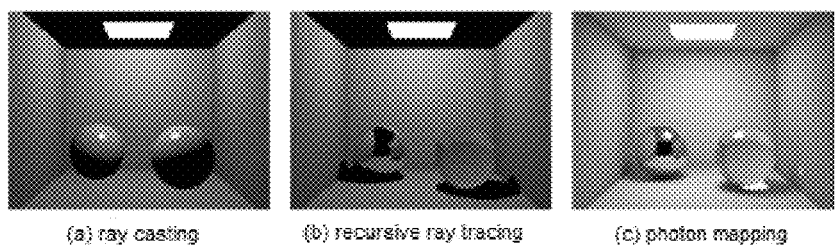
FIG. 13 shows various illumination models.
Figure 14:
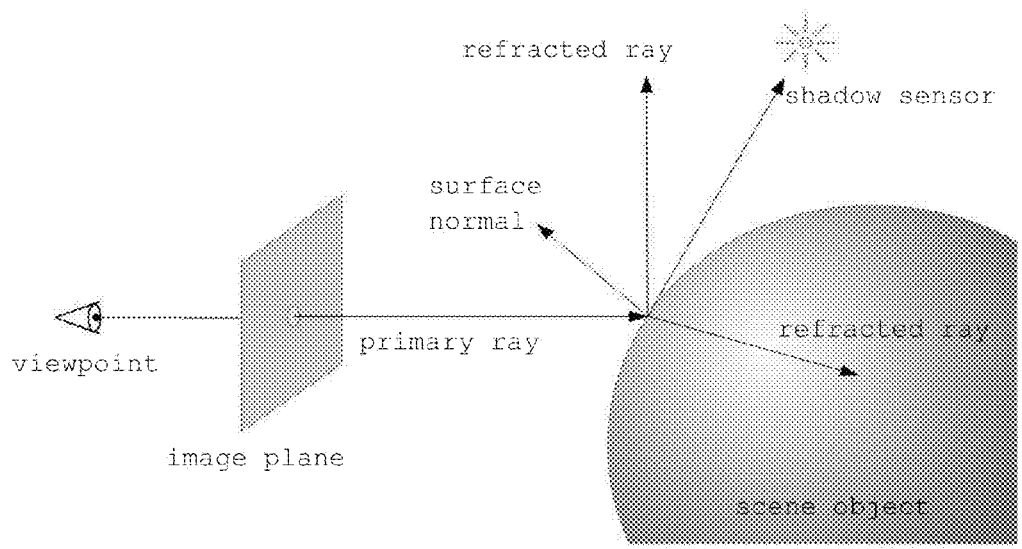
FIG. 14 shows a global illumination model.

For a visual comparison between the different illumination models see also FIGS. 13 and 14.

6.4 Implemented Acceleration Methods

As has already been mentioned in Section 6.1.4, several methods of acceleration were examined and implemented. Initially, the step size of each ray was set to one voxel during ray casting. In other words, each adjacent voxel was checked. First acceleration was carried out by means of empty space skipping (ESS). In this case, the ray is not traced voxel by voxel, but skips larger distances (in our case the distance of half truncation). Not every adjacent voxel therefore has to be checked. Should a zero crossing be identified, the procedure is continued voxel by voxel until the surface has been found.

The acceleration method presented by Samet and Kochut [16] using an octree was also examined. Put simply, the voxels in a region without a surface present are combined and a tree is thus formed. The further the distance from the surface, the greater are the combined regions. The individual voxels immediately in front of the surface are not combined. With ray casting, the ray can therefore initially penetrate larger regions and thus "advance" more quickly towards the actual surface.

This algorithm indeed constitutes an acceleration, however this tree would have to be rebuilt again with each run during the scanning process. Currently this algorithm is not used for the scanning process. This method can certainly result in an acceleration when it comes to the trackball functions (rotation, zooming and scrolling the model in the pause mode), since the tree has to be built only once in this case.

Figure 15:
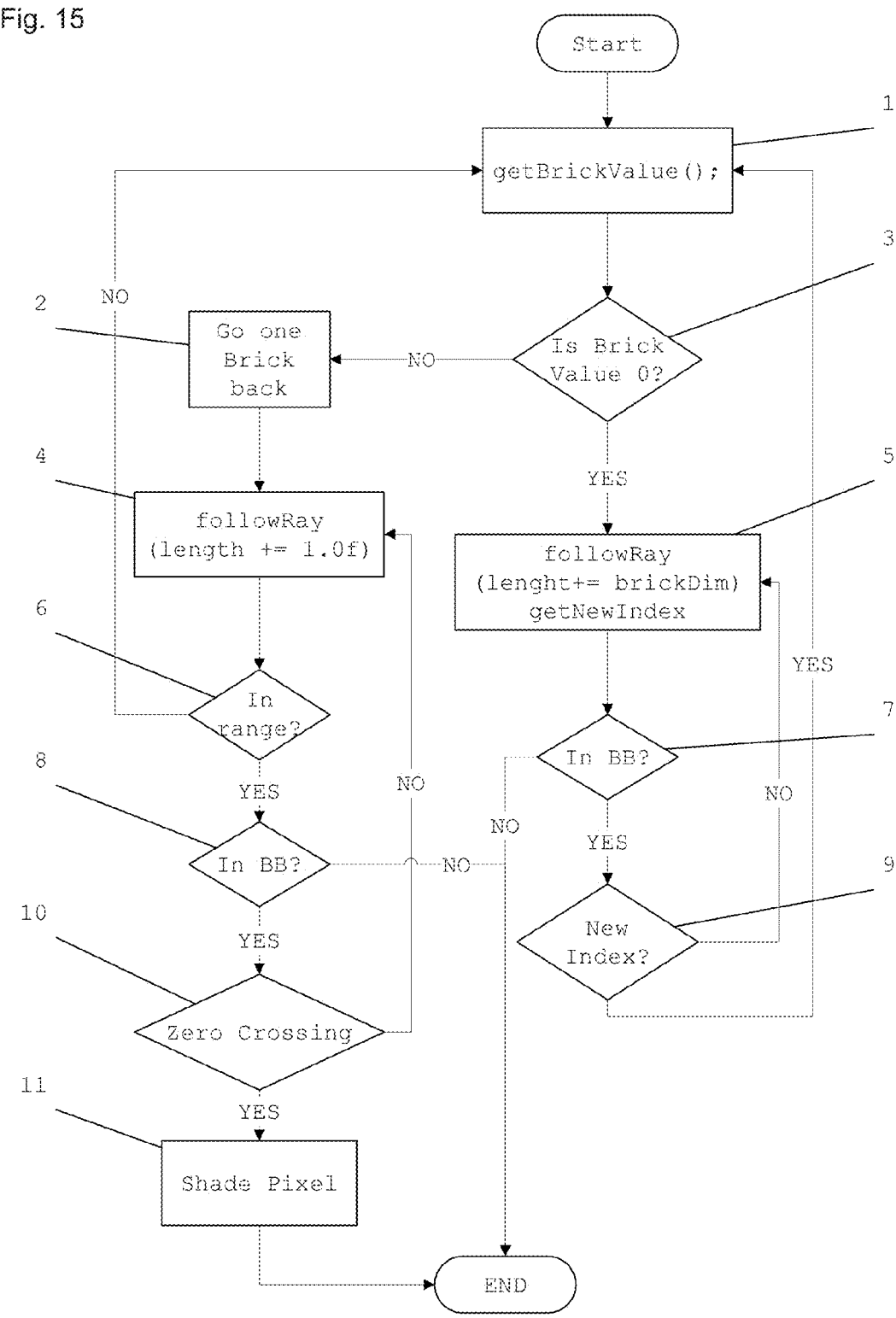
FIG. 15 shows workflow of the optimized raycaster.

Besides ESS, brick empty space skipping (BESS) was also implemented. As explained in Section 4.5, "bricks" are described during the TSDF updates. The described bricks are used in the raycaster in order to carry out further skips. The individual rays now pass through the brick cube and check whether or not a surface is present in the bricks through which the rays have passed. If a brick is occupied (the respective TSDF voxels contain a zero crossing and therefore a surface), the ray length is reduced again by one skip (brick length), since otherwise the surface can be skipped. Once a return has been performed, the procedure is continued again in small steps (voxel by voxel) in order to find the surface. This accelerates the raycaster considerably. Should the ray pass by an inclined surface in parallel, this acceleration method is nullified, since the bricks indeed indicate that a surface is in the vicinity, but it is not (yet) being illuminated. For such cases, this algorithm has been expanded somewhat; the workflow can be seen in FIG. 15. Should a brick with a surface be found, this is searched for the distance $\sqrt{3.0} \cdot i32BRICK_{VOXELGRID_{DIM}} + i32BRICK_{VOXELGRID_{DIM}}$ (this corresponds to the spatial diagonal of one brick plus one brick length due to the skip length). Should no surface be found within this distance, the step size is increased again until the next brick with a surface has been found. In FIG. 15, this test described above takes place in the query 'In range?' (see step 6 in FIG. 15).

A further optimization during the scanning process is the reduction of the length of the ray. The rays are not launched in the projection center, but instead, since no elements can be found up to the cover glass, the rays are launched just in front of the glass. The length of the rays can also be varied, with the result that the ray is not traced as far as the end of the bounding box. This implementation in the raycaster again gave a performance gain of up to 10%.

6.5 Coloring

The shading technology has already been discussed in Section 6.3. Here, an implemented extension is explained. As is known from Section 4.3, each TSDF value receives a weight. This weight is used in the coloring. Should the weight be low (first scan, . . . ) the pixels are colored in a predefined color (defined as ucSTART_COLOR_R, ucSTART_COLOR_G, ucSTART_COLOR_B, ucSTART_COLOR_A), with a higher weight the color of the surface increasingly approaches the defined end color (defined as ucEND_COLOR_R, ucEND_COLOR_G, ucEND_COLOR_B, ucEND_COLOR_A), and from a certain weight (defined in f32GOOD_MEASUREMENT_WEIGHT) the predefined "good" color(defined as ucGOOD_COLOR_R, ucGOOD_COLOR_G, ucGOOD_COLOR_B, ucGOOD_COLOR_A) is used. The user can thus identify which locations have been scanned sufficiently often.

The coloring occurs in the method void shadePixel(int index, floatfNormalVector, const float fLightDirection, floatfAlpha, _global unsigned char* pixel, _global unsigned char* ucRenderWindowCharArray, short sWeight) in the file 'raycaster.cl'. Should the value "fAlpha" be 0.0, then the current pixel is set to the background. If not, the color is determined Should the weight (sWeight) be greater than or equal to i32MAX_VOXEL_WEIGHT−1, the pixel is set to the "good color". Otherwise, a mean value is calculated by means of

```
1 // Start and end color of color gradient
2 float4 f4Start = (float4) (ucSTART_COLOR_R,
  ucSTART_COLOR_G, ucSTART_COLOR_B,
  ucSTART_COLOR_A);
3 float4 f4End = (float4) (ucEND_COLOR_R, ucEND_COLOR_G,
  ucEND_COLOR_B, ucEND_COLOR_A);
4
```

Since the light does not impinge uniformly on a curved surface and therefore everywhere received the same color, the angle of incidence is now determined using the surface normals:

```
1 float fCosinusPhi = fabs(fNormalVector[0] * fLightDirection[0] +
2                          fNormalVector[1] * fLightDirection[1] +
```

This angle calculation is required so that the appropriate color can be determined by means of

```
1 // shade color (excl. Alpha)
2 f4Color.xyz = f4Color.xyz * fCosinusPhi;
```

The final color value is then stored in the variable f4Color.

7. Scan Resume

In an intraoral scan situation the registration will frequently lose track of the scanner position (because of quick movement or poor input data). If this happens the system will continue to process the incoming depth data, try to find a matching camera position and pick up scanning again

7.1 Scan Pose Candidate Selection: Check Vertex in Brick

Instead of traversing the TSDF volume to extract a surface and generating a normal and vertex to be matched using an ICP algorithm this method works the other way around by projecting the current depth image samples into the volume.

A pose (transformation matrix) is tested by applying it to the vertex map of the current depth image prior to using it for an ICP registration attempt. If the tested pose exactly matched the actual scanner pose, all transformed valid vertices would be located near to the stored model surface.

As an exact match is unlikely to happen, this can only provide a measure for finding close to fit poses: The more of the tested "global" vertex coordinates lie close to a scanned surface the more likely it might be close to fit and a good candidate for an ICP registration attempt.

The GPU kernel is parallelized upon the poses to be checked (one work group per pose). To be able to sum up the inliers for a tested pose all work items for this pose must be within the same work group to be able to correctly calculate the local sum.

Further information concerning parallelization can be found in [21] and [7].

All work groups will use its assigned pose to transform all vertices, check corresponding brick values and produce the amount of inliers for the tested pose with work items performing the following steps:

1. Fetch pose[group#]
2. Loop through vertex map (work group size chunks in parallel)
   a. Transform vertex to global using pose
   b. Check brick value (if global position inside volume)
   c. Increment private counter, if it's a surface brick
3. Sum up private counters using shared memory (prefix sum)
4. First item of work group: write sum to inliers[group#]

After kernel execution the inlier array is read back to the host. The host can examine the result and mark the poses with the highest inlier count as candidates for an ICP registration attempt. See also FIG. 16.

7.2 Scan Control Thread

This method can be integrated into the scan control thread as shown in FIG. 17.

During normal scanning the control thread will stay in the left hand side (steps 12 to 22 in FIG. 17) and loop through the following steps to construct the model:

1) Obtain a new depth image
2) Evaluate associated position for depth image by comparing it with raycasting output of the previous cycle
3) Update model using new position and depth image
4) Raycast updated model from the new position In case the system lost track of the scanner's position (previous registration attempt failed) the model cannot be updated. The next depth image information is used to check previous positions against the model to find a good candidate for a new registration attempt. If a candidate has been found it is used for the next registration attempt. If the registration is successful the scan is resumed normally using this position, otherwise the next depth image will be used for candidate selection again.

Once started the scan control thread enters an endless loop (see FIG. 18), unlocks the semaphore for access to system variables and parameters and suspends until a run semaphore is unlocked. Scanning is enabled (see FIG. 18a) or resumed (see FIG. 18b) by setting the enable flag (step 33) first, then unlocking both semaphores (data access and run, steps 34 and 35). The thread will suspend again if the enable flag is cleared (step 37). To ensure the thread is already suspended and it is safe to access its data wait till the data access semaphore is unlocked by the thread (step 38).

7.3 Expanding Flexibility by Adding "Synthetic Poses"

A scan resume position is likely to be somewhere on the path the scanner has been moving before: the scanner could physically move along this path (empty space, no obstruction, see also section 4.7) and generated model data from the viewpoints along this path that can be extracted again for matching with new data. Therefor the most obvious choice for the candidate pool is using the registered camera poses generated prior to the scan interruption.

This will enable resuming anywhere close along the path, but however, if the scanner is placed with a different elevation from the model surface or in a different orientation (for example rotated by 180°) this approach will fail to find an appropriate candidate.

Fortunately the poses check method is not constraint to use these recorded poses only. In fact the input could be any set of arbitrary poses, but it is impossible to resume at poses that do not point on any previously measured surface or at poses that are actually behind the surface and eventually inside the scanned object. So the most useful poses are located in the vicinity of the scan path by creating variations of the recorded poses.

If the scan resume is required to support picking up again after the hand piece has been rotated by 180° at the front of the jaw to scan the second half, a 180° rotation around the camera view direction can be applied to scan poses to generate new hypothetical candidates that might produce a match in this situation. This can be applied to all recorded poses if necessary, thus having twice the amount of poses in total, but the ability to pick up after an 180° turn anywhere along the path.

This approach might be further extended to generate multiple synthetic poses from each recorded camera pose using a combination of different angle rotations around different axis. Additionally different translation can be applied too, thus covering the possibility of picking up even if the distance to the model differs significantly from the distance in the recorded path.

A large amount of variation can be generated, eventually producing too many poses to be feasible. The vertex map could be subsampled to reduce the computational effort, thus compromising accuracy of the results. Variations might be applied only to a subset of the recorded poses (either last n poses or random pick or a combination of both). The amount of camera poses might be reduced beforehand by only recording poses that differ significantly from the previous recorded pose.

After all it is still a brute force method which could be enhanced if additional (other) information, especially non-visual sensor-data (for example accelerometer data) is used to reduce the number of possibilities. However, brute force methods tend to gain suitability with time due to constantly growing computer performance.

Another embodiment of the invention is a non-transitory computer readable medium containing computer code (software) that when executed on a computer causes the computer to execute the methods disclosed above. The programmed computer may be in the form of a computerized controller.

BIBLIOGRAPHY

[1] T. Bach. Gpu-based volume ray casting with advanced illumination. Seminar paper, RWTH Aachen, 2009.
[2] R. Brent. Algorithms for minimization without derivatives. Book, Dover Publications, 2002.
[3] A. Neubauer et al. Cell-based first-hit ray casting. Proceedings of the Symposium on Data Visualization 2002, pages 77 et seq 2002.

[4] G. Marmitt et al. Fast and accurate ray-voxel intersection techniques for isosurface ray tracing. VMV, 2004.
[5] M. Hadwiger et al. Real-time ray-casting and advanced shading of discrete isosurfaces. EUROGRAPHICS 2005, volume 24(2005), Number 3, 2005.
[6] N. Tatarchuk et al. Real-time isosurface extraction using the gpu programmable geometry pipeline. Advanced Real-Time Rendering in 3D Graphics and Games Course, chapter 9—SIGGRAPH 2007, 2007.
[7] R. A. Newcombe et al. Kinectfusion: Real-time dense surface mapping and tracking. ISMAR, 2011.
[8] S. Parker et al. Interactive ray tracing for isosurface rendering. Proceedings of Visualization, 1998.
[9] W. Press et al. Numerical recipes in c++. Book, Cambridge University Press, 2002.
[10] P. Frey. Raycasting von adaptiven Isoflächen. Term paper, ETH Zurich, 2005.
[11] S. F. Frisken and R. N. Perry. Efficient estimation of 3d Euclidean distance fields from 2d range images. Proceedings of the IEEE Symposium on Volume Visualization and Graphics, 2002.
[12] R. Hagan and C. Braley. Numerical methods for isosurface volume rendering. Virginia Tech 2009, 2009.
[13] H. Mühlensiepen. Visualisierung von magnetohydrodynamsichen Daten. Dissertation, F H Aachen, 2004.
[14] Heinrich Müller and Michael Wehle. Visualization of implicit surfaces using adaptive tetrahedrizations. Scientific Visualization Conference, 1997.
[15] Szymon Rusinkiewicz and Marc Levoy. Efficient variants of iterative closest point algorithm, June 2001.
[16] Hanan Samet and Andrzej Kochut. Octree approximation and compression methods. In 3*DPVT*, pages 460-469, 2002.
[17] NXP (Philips Semiconductors). The i²c specification. http://www.nxp.com/documents/other/39340011.pdf. As of: January 2000.
[18] C. Sigg. Representation and rendering of implicit surfaces. Dissertation, ETH Zurich, 2006.
[19] M. Tauer Implementation eines Raytracers innerhalb der 3D Plattform GroIMP. Student research project, TU Cottbus, 2006.
[20] Harvey E. Cline William E. Lorensen. Marching cubes: A high resolution 3d surface construction algorithm. Computer Graphics, 1987.
[21] The open standard for parallel programming of heterogeneous systems http://www.khronos.org/opencl/. As of: July 2013.

The invention claimed is:

1. A method of capturing three-dimensional (3D) information on a structure, comprising:
obtaining a first image set containing images of the structure with at least one physical camera located at a first position, the first image set comprising one or more images;
reconstructing 3D information from the first image set;
obtaining 3D information from a virtual camera out of an existing global model of the structure;
determining correspondences between the obtained 3D information and the reconstructed 3D information;
determining camera motion between the obtained 3D information and the reconstructed 3D information from said correspondences; and
updating the existing global model by entering the obtained 3D information using the determined camera motion.

2. The method of claim 1, wherein the structure is a natural structure.

3. The method of claim 1, wherein the structure is an artificial structure.

4. The method of claim 1, wherein the structure is an artificial intra-oral structure.

5. The method of claim 1, wherein said virtual camera is provided by projecting an existing three-dimensional model using raycasting.

6. The method of claim 5, wherein said raycasting employs a previous camera position from which a previous image set of 2D images was taken.

7. The method of claim 5, wherein said raycasting employs a synthetic camera position.

8. The method of claim 7, wherein said synthetic camera position is generated by applying geometric transformations on a previous camera position from which a previous image set of 2D images was taken.

9. The method of claim 1, wherein said obtained 3D information derived by the virtual camera is unequal in size with the 3D information reconstructed out of said first image set.

10. The method of claim 1, wherein said obtained 3D information derived by a virtual camera is equal in size with the 3D information reconstructed from said first image set.

11. The method of claim 1, wherein said camera motion is described by a translation vector and a rotation matrix.

12. The method of claim 1, wherein said steps are repeated with a second image set by:
with the at least one physical camera located at a second position, obtaining the second image set containing at least one image of the structure, the second position being different from the first position;
reconstructing further 3D information from said second image set;
obtaining further 3D information from the virtual camera out of the existing global model of the structure;
determining a correspondence between the obtained further 3D information and the reconstructed further 3D information;
determining further camera motion between the obtained further 3D information and the reconstructed further 3D information from said correspondences; and
updating the existing global model by entering the obtained further 3D information using the determined further camera motion.

13. The method of claim 1, wherein each camera position is stored.

14. The method of claim 13, wherein according to said stored camera positions, an empty space is defined that cannot be updated.

15. The method of claim 1, wherein each derived camera motion is stored.

16. A non-transitory computer readable medium containing computer code that when executed on a computer causes the computer to execute the method of claim 1.

* * * * *